(12) United States Patent
Ploechinger

(10) Patent No.: US 8,841,115 B2
(45) Date of Patent: Sep. 23, 2014

(54) INSULATION PANEL

(71) Applicant: Heinz Ploechinger, Freinberg (AT)

(72) Inventor: Heinz Ploechinger, Freinberg (AT)

(*) Notice: Subject to any disclaimer, the term of this patent is extended or adjusted under 35 U.S.C. 154(b) by 0 days.

(21) Appl. No.: 14/229,846

(22) Filed: Mar. 29, 2014

(65) Prior Publication Data

US 2014/0212623 A1 Jul. 31, 2014

Related U.S. Application Data

(62) Division of application No. 13/083,519, filed on Apr. 8, 2011, now Pat. No. 8,685,707.

(60) Provisional application No. 61/354,665, filed on Jun. 14, 2010, provisional application No. 61/380,253, filed on Sep. 5, 2010.

(51) Int. Cl.
| | | |
|---|---|---|
| *C12N 1/12* | (2006.01) | |
| *B32B 1/04* | (2006.01) | |
| *B32B 3/02* | (2006.01) | |
| *B32B 5/12* | (2006.01) | |
| *B32B 3/12* | (2006.01) | |
| *E04B 1/90* | (2006.01) | |
| *E04B 1/76* | (2006.01) | |
| *E04B 1/74* | (2006.01) | |

(52) U.S. Cl.
CPC ... *E04B 1/90* (2013.01); *B32B 3/12* (2013.01); *E04B 2001/748* (2013.01); *E04B 1/7604* (2013.01)
USPC ........... 435/257.1; 428/76; 428/113; 428/116

(58) Field of Classification Search
CPC ......... A01G 33/00; H01M 2/18; Y02E 60/12; A01H 4/001; B09B 3/0025; B32B 2250/02; B32B 2250/20; B32B 2255/02; B32B 2262/062; B32B 2307/7163; B32B 2307/7265; B32B 23/12; B32B 2439/40; B32B 2439/70
See application file for complete search history.

(56) References Cited

U.S. PATENT DOCUMENTS

| | | | |
|---|---|---|---|
| 3,768,200 | A | 10/1973 | Klock |
| 4,214,027 | A | 7/1980 | Knuaf et al. |
| 5,779,960 | A | 7/1998 | Berlowitz-Tarrant et al. |
| 5,852,077 | A | 12/1998 | Zawada et al. |
| 5,979,363 | A | 11/1999 | Shaar |
| 2005/0009208 | A1 | 1/2005 | Carpenter |
| 2006/0275563 | A1 | 12/2006 | Duffy |
| 2009/0148927 | A1 | 6/2009 | Schroeder et al. |
| 2009/0294354 | A1 | 12/2009 | Theodore et al. |
| 2010/0021968 | A1 | 1/2010 | Hu et al. |
| 2010/0297436 | A1 | 11/2010 | Mahan |

OTHER PUBLICATIONS

Dictionary entry "Algilit", retrieved from website http://www.wissenschaft-online.de/abo/lexikon/bio/2051 on Mar. 4, 2011.

*Primary Examiner* — Chris R Tate
*Assistant Examiner* — Douglas F White
(74) *Attorney, Agent, or Firm* — Smartpat PLC; Axel Nix

(57) ABSTRACT

The present disclosure describes use of filamentous algae to form insulating construction materials which provide thermal and noise insulation. Algae from the order Zygnematales, the Cladophorales, or the Ulotrichales can be dried and formed for use as insulating material. Algae mass can be combined into several layers, using a binder to attach the layers to each other. A composite material of algae mass and an additive can be used and form the body of insulation panels having honeycomb-shaped chambers, which are sealed by a foil that is laminated onto the body.

11 Claims, 28 Drawing Sheets

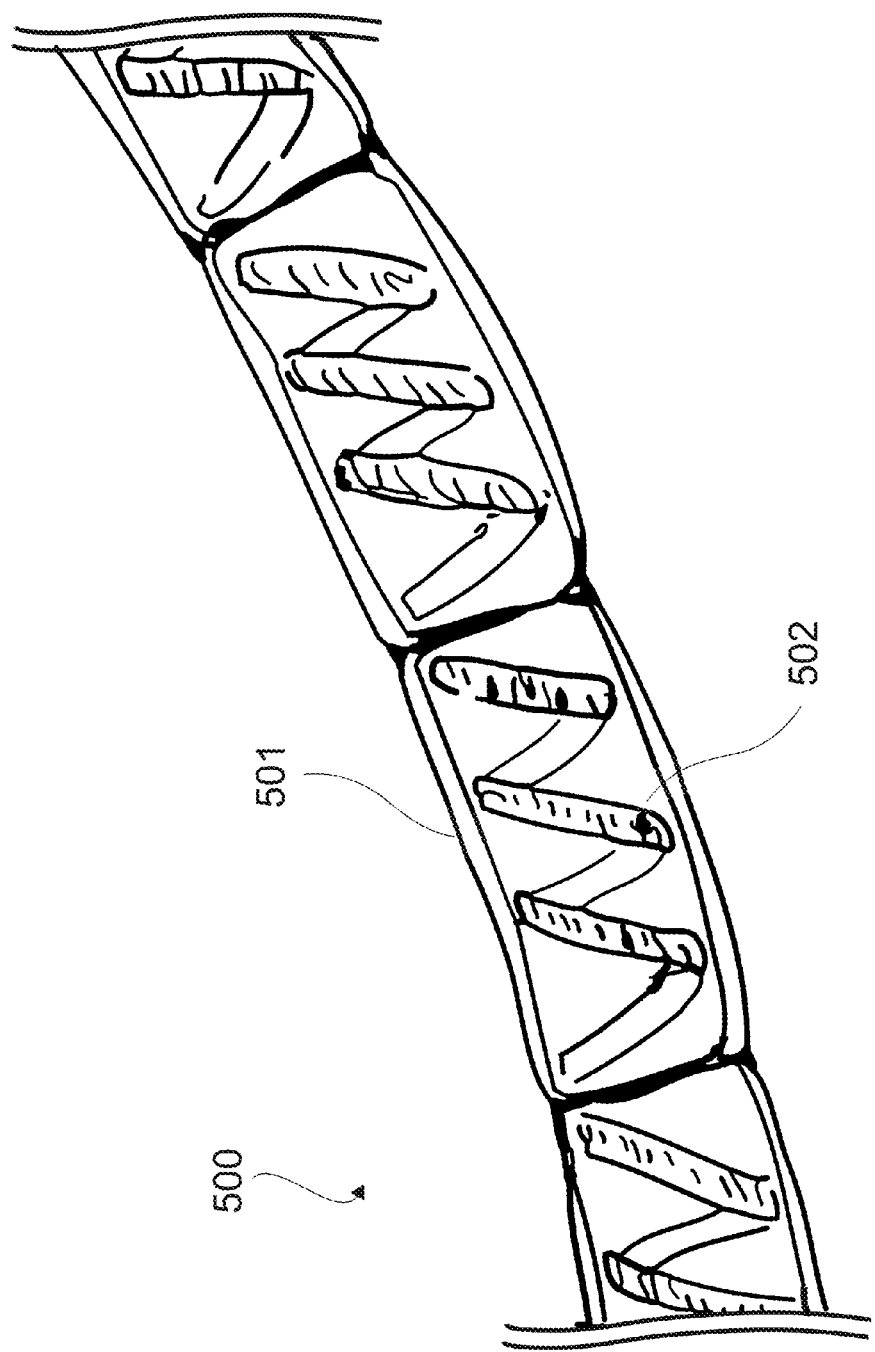

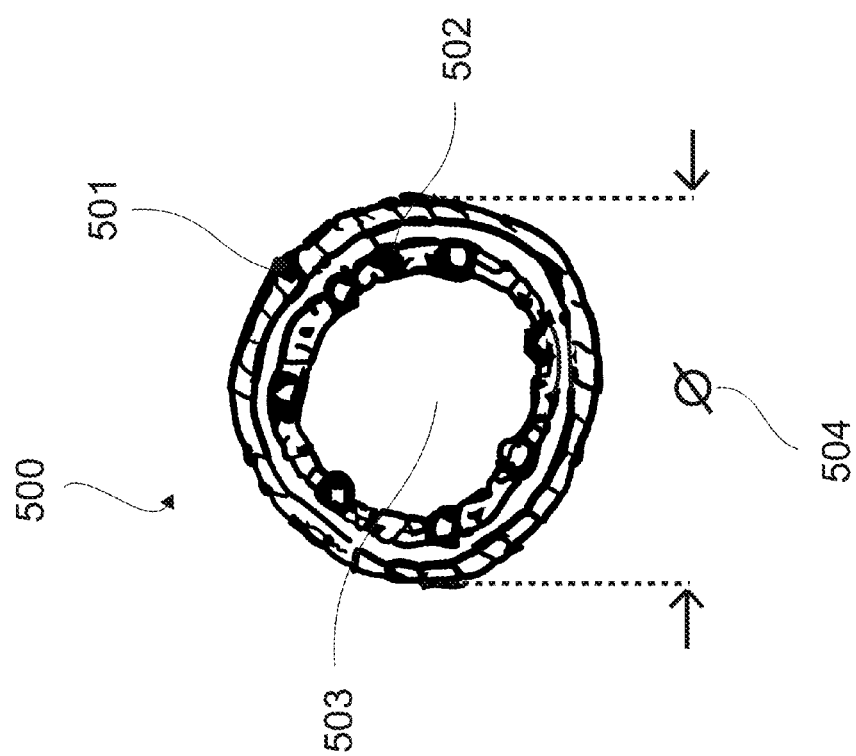

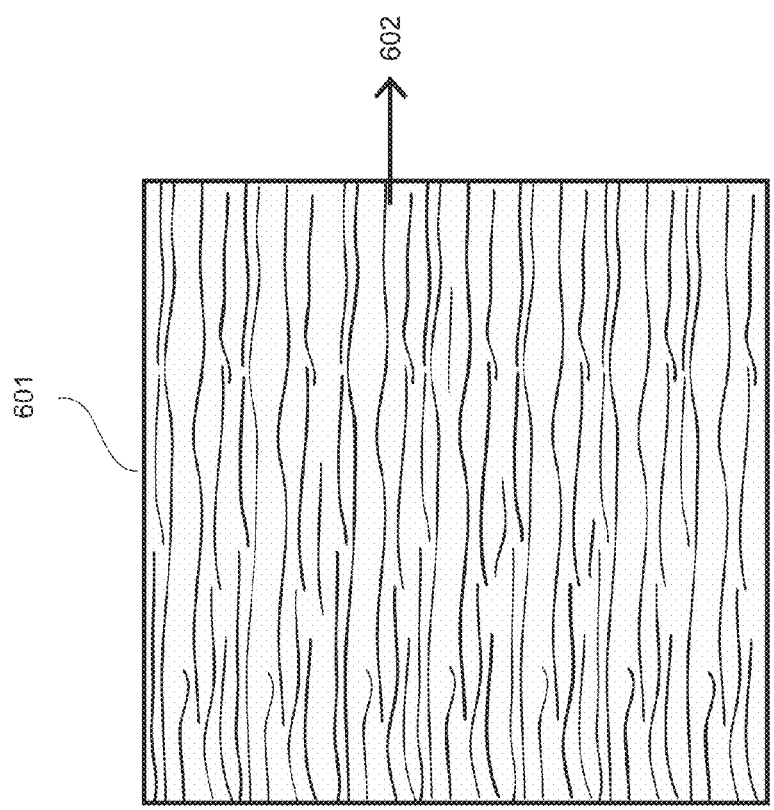

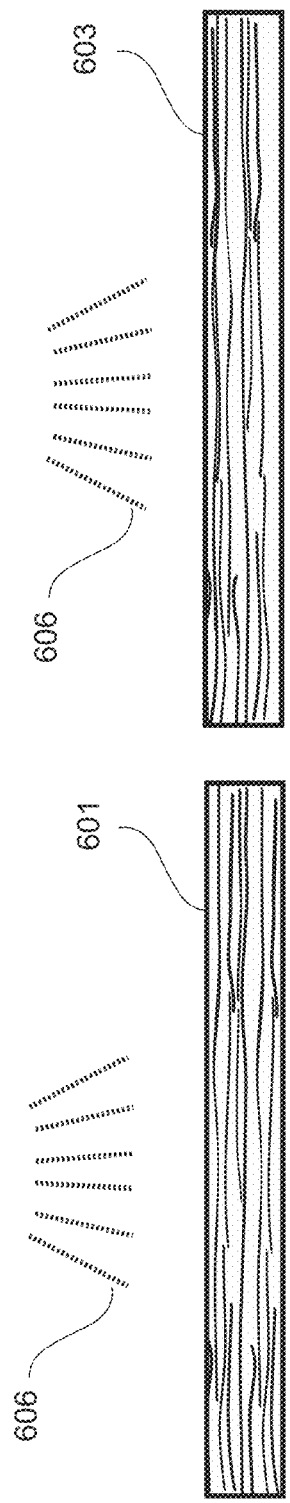

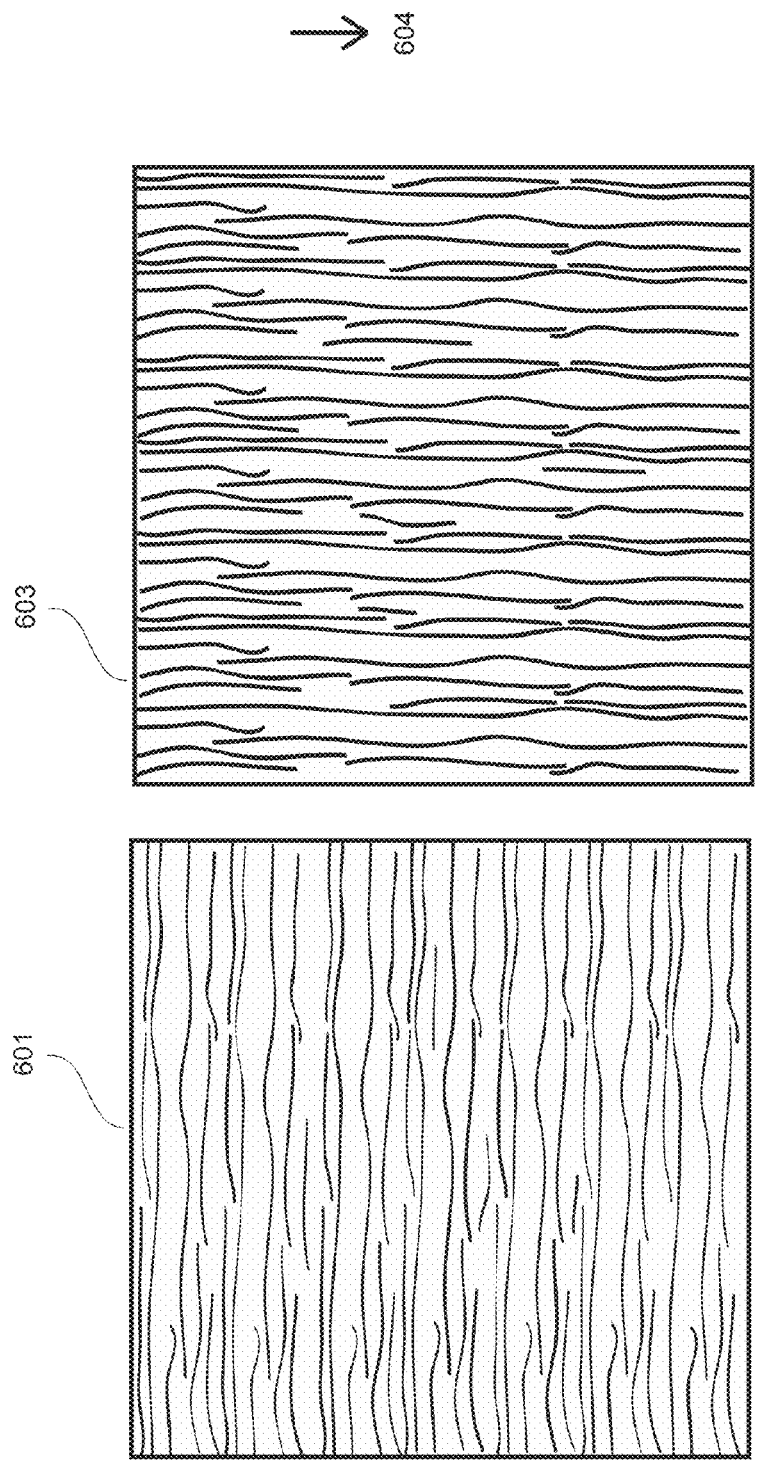

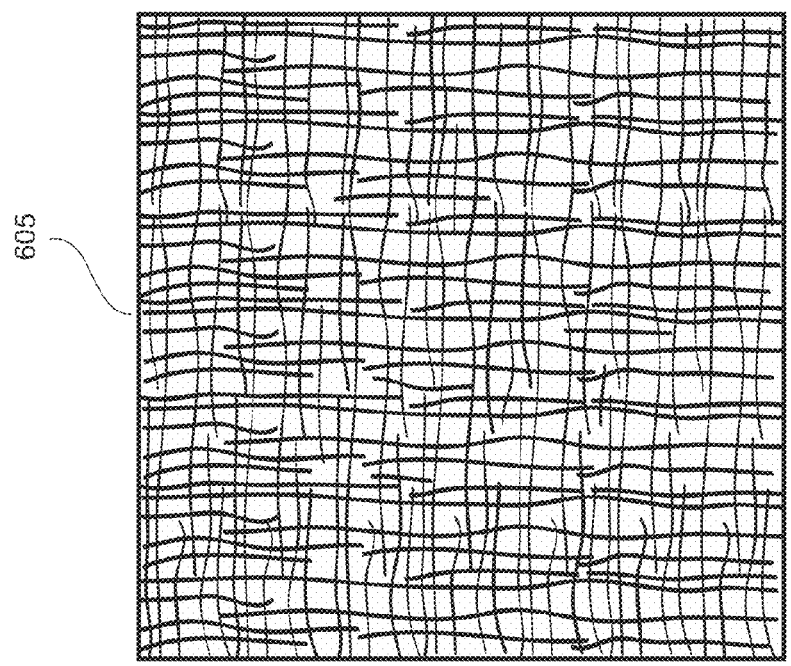

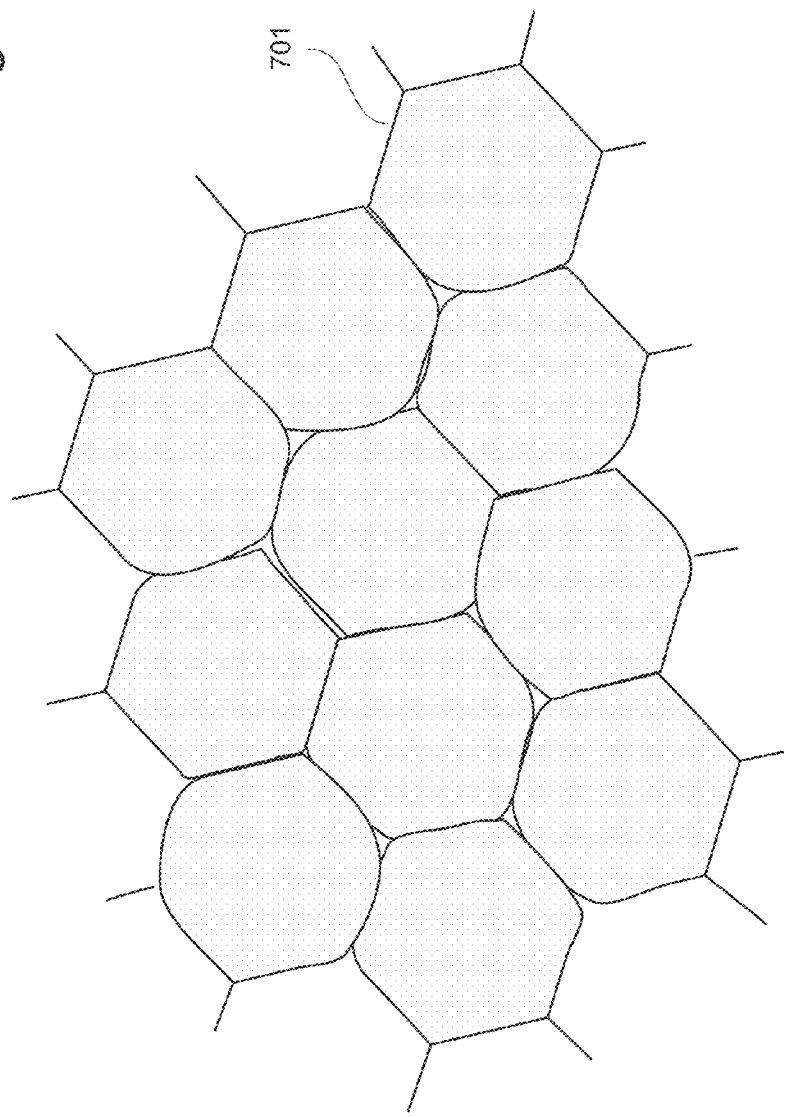

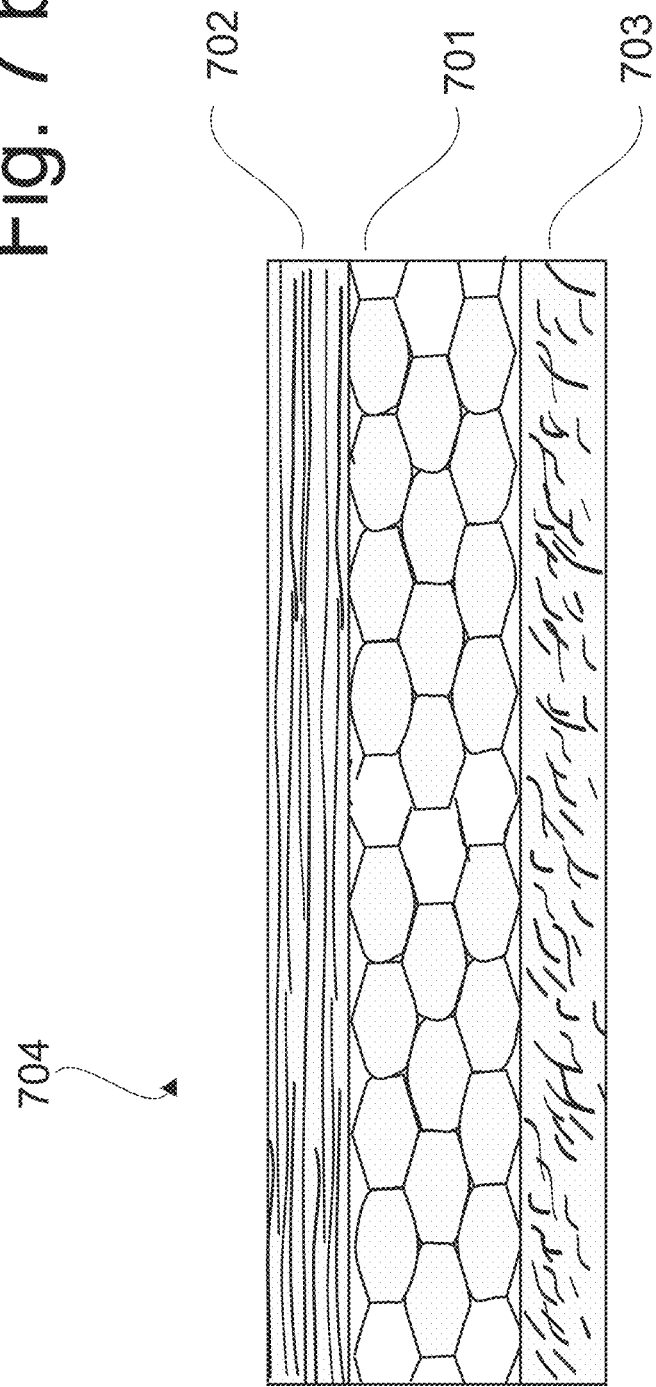

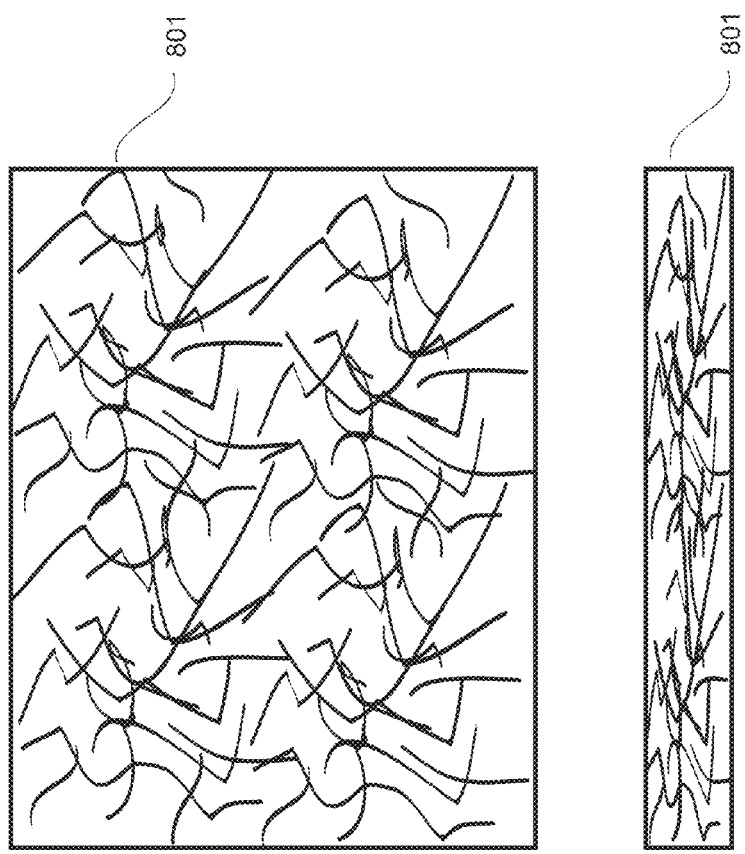

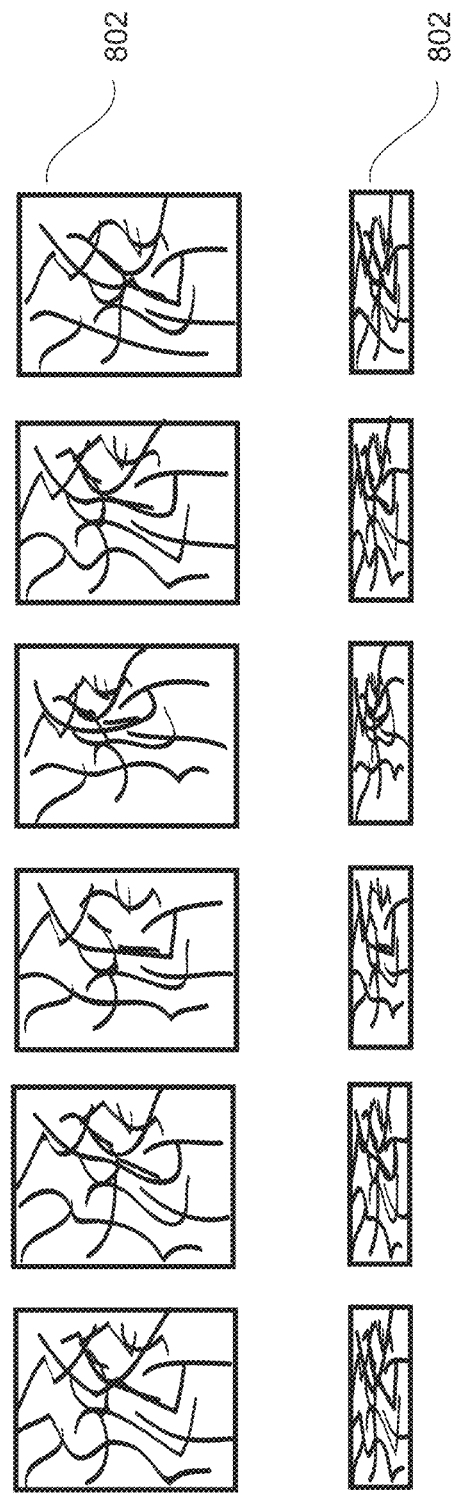

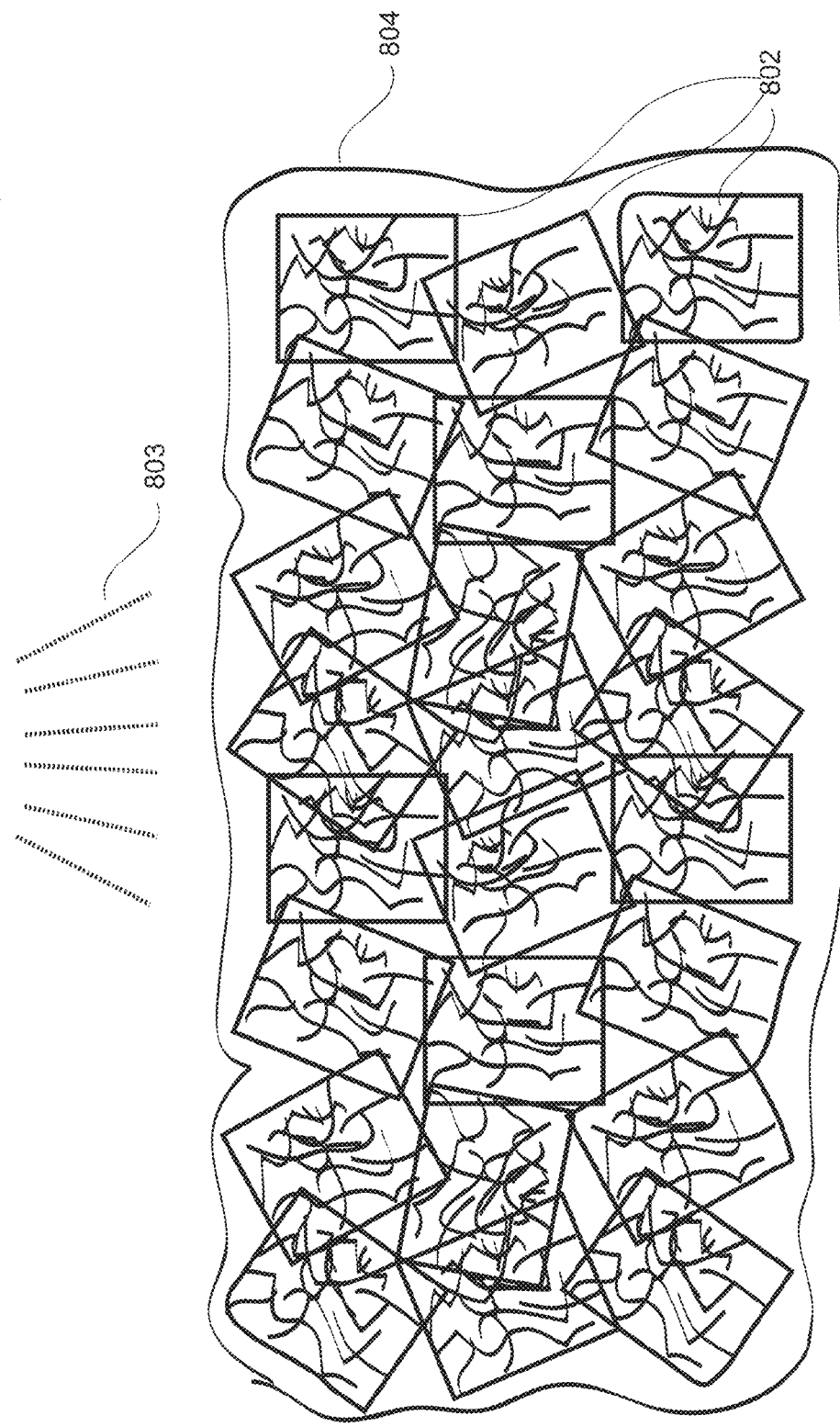

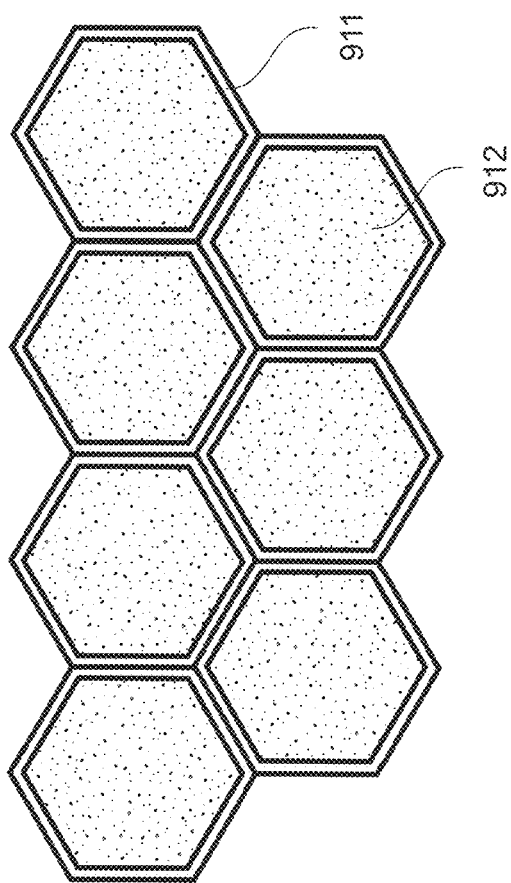

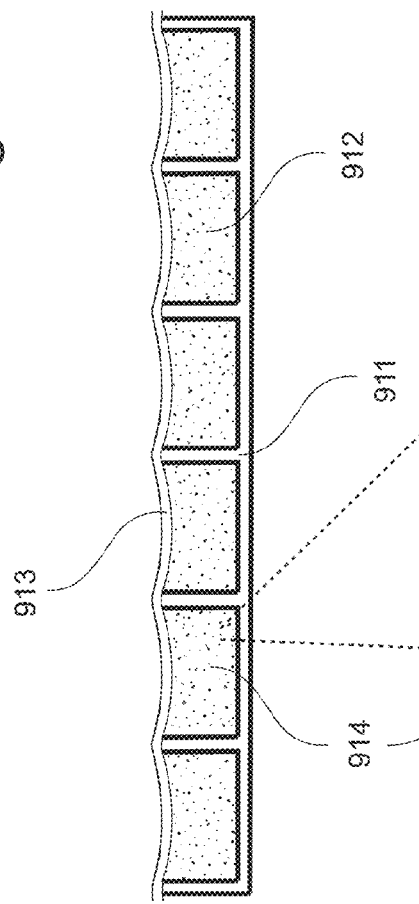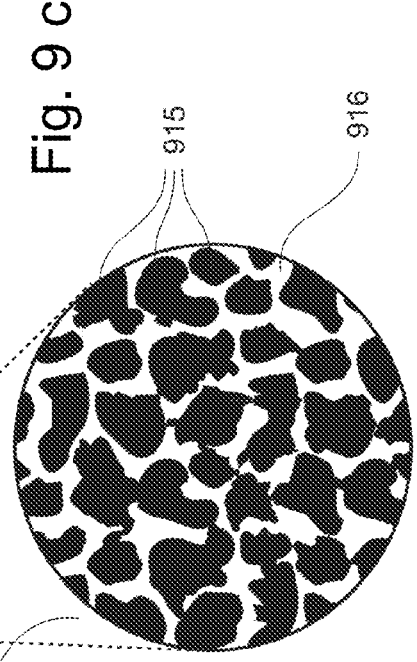

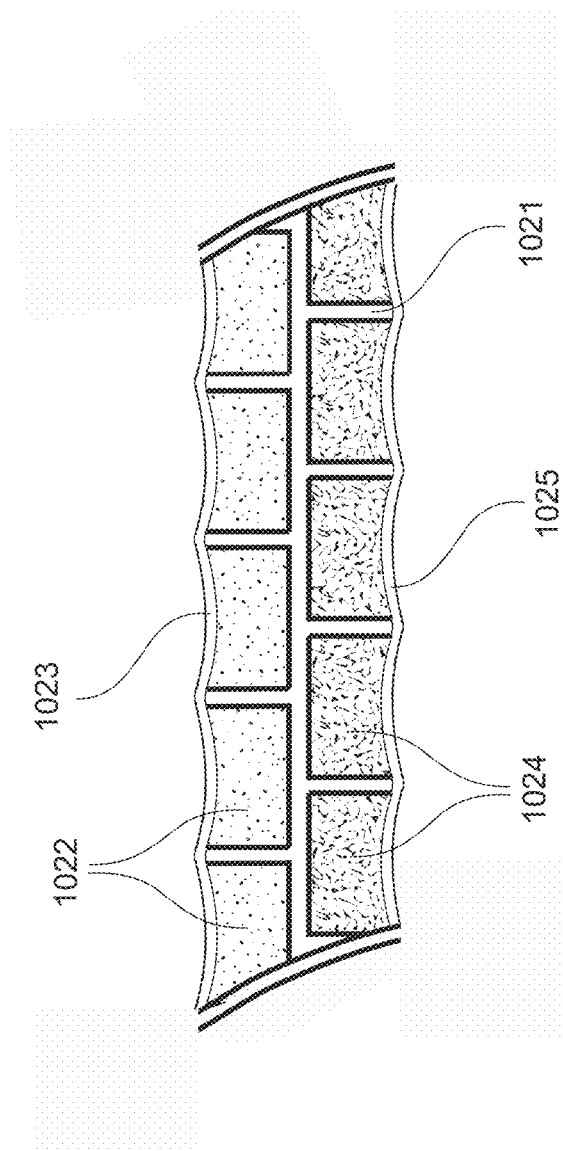

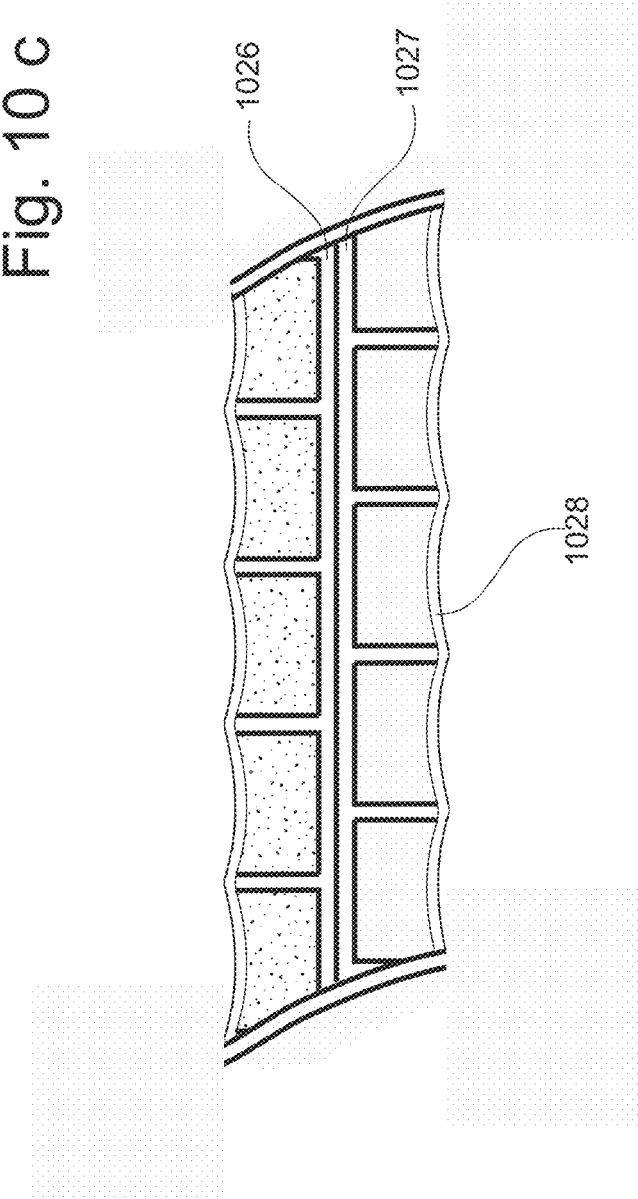

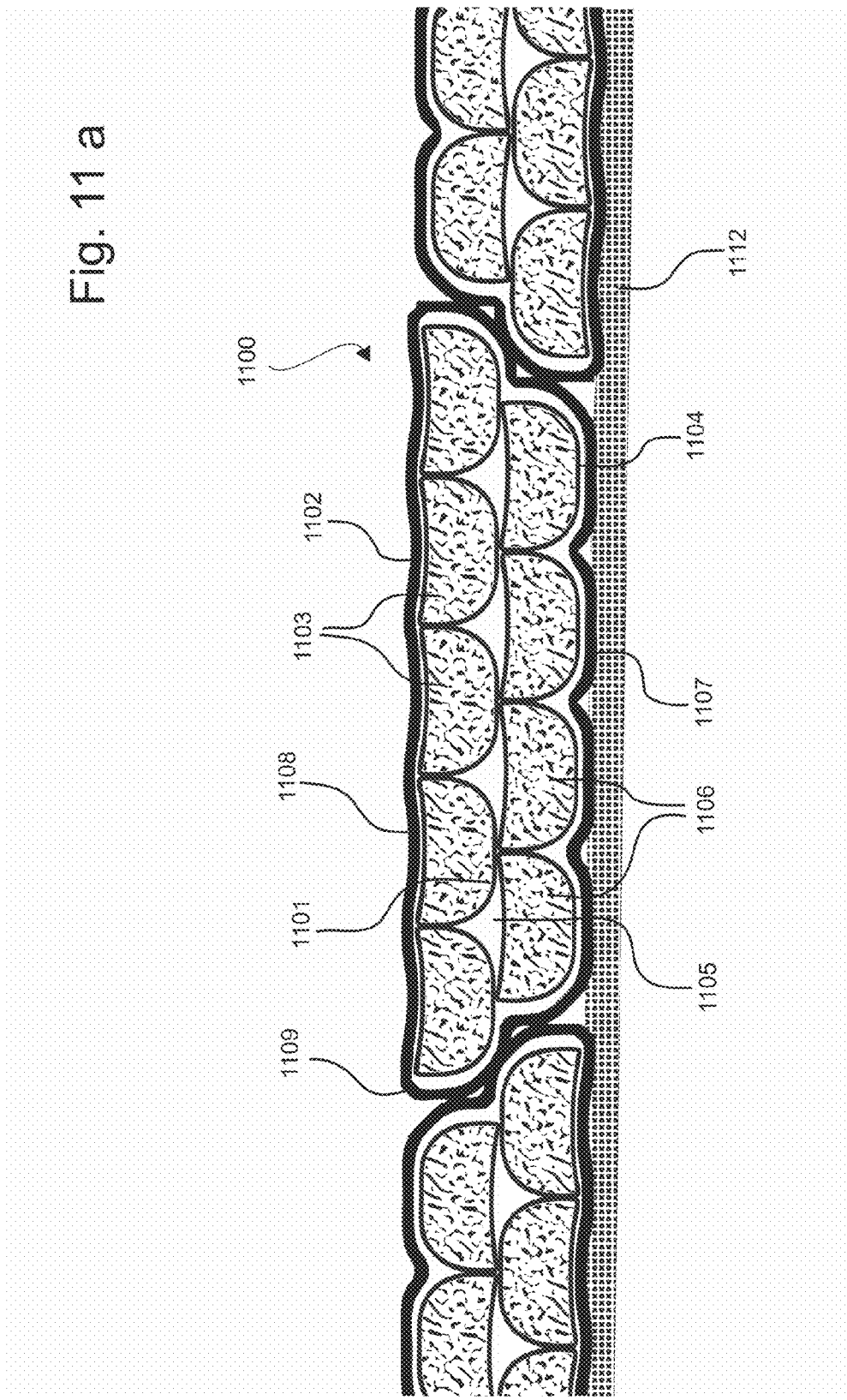

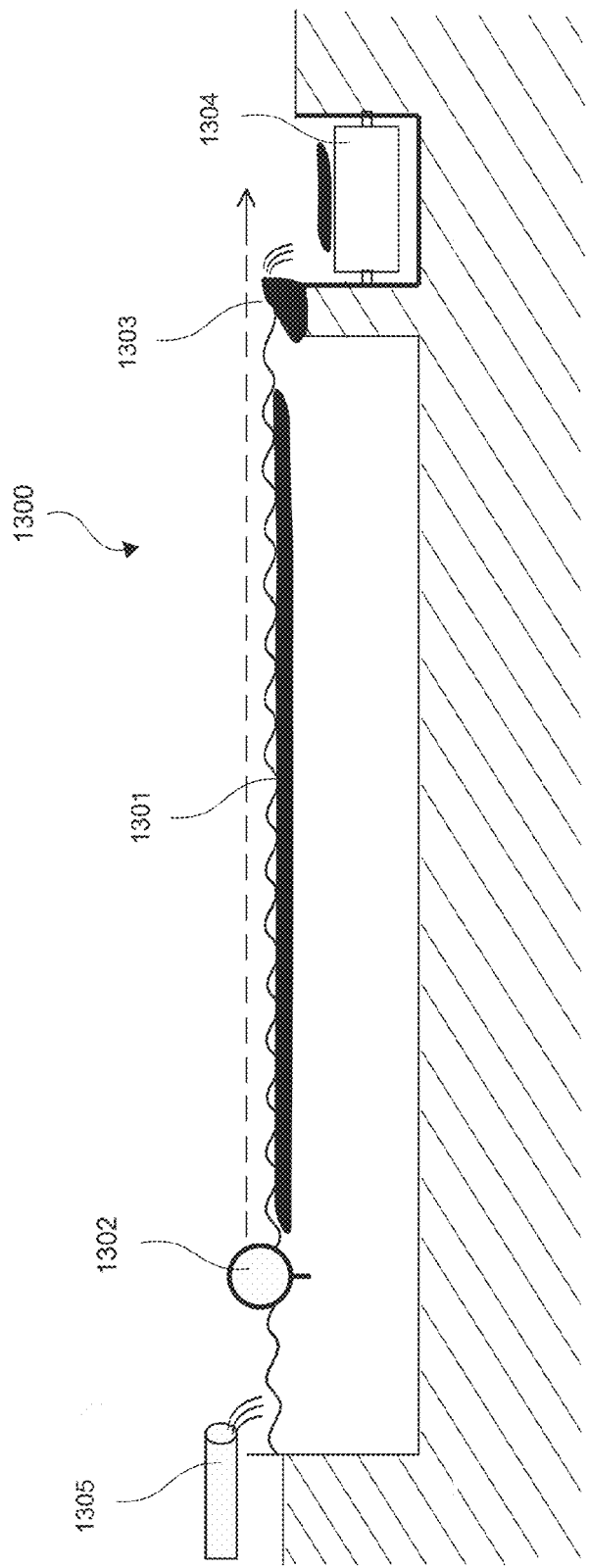

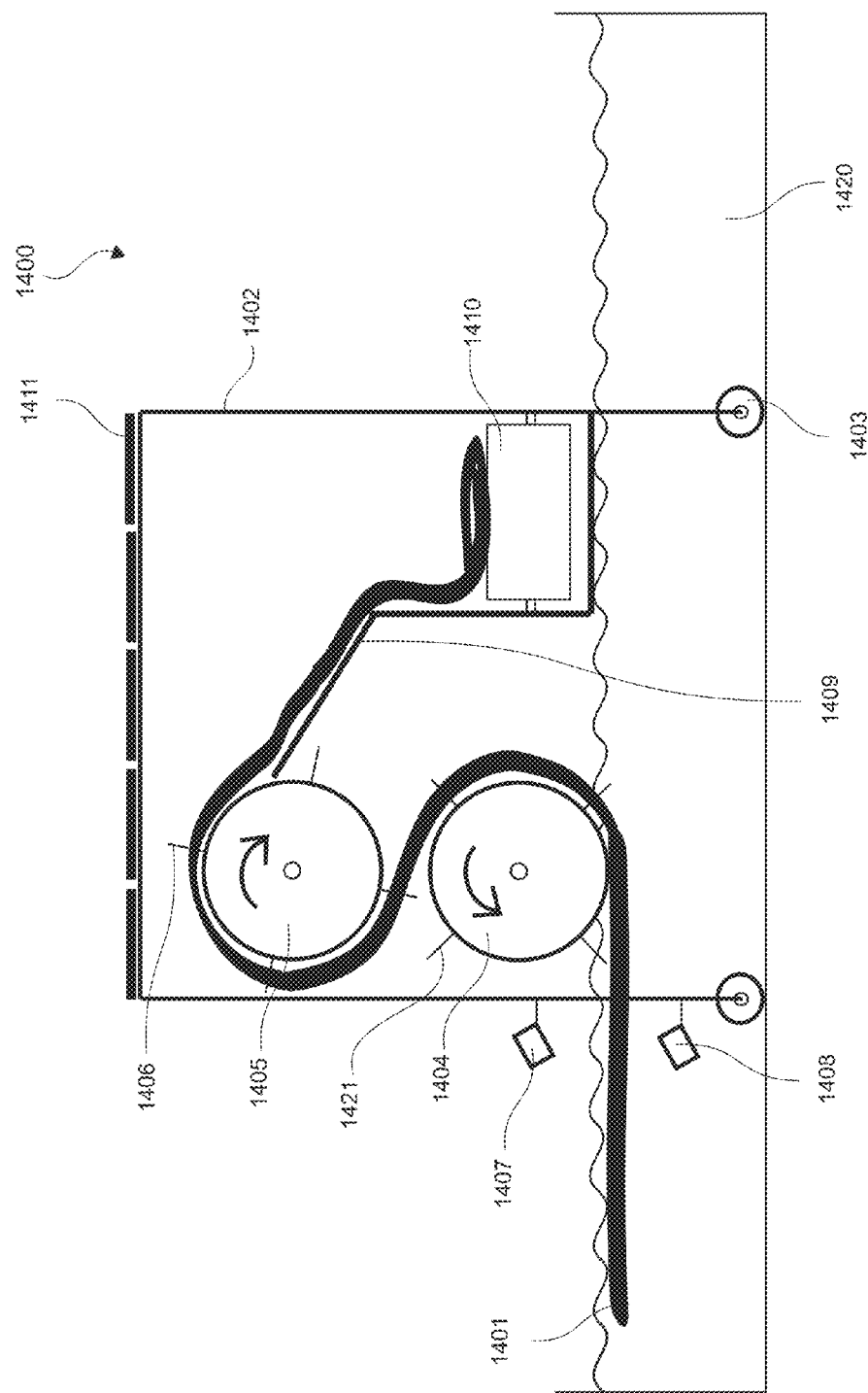

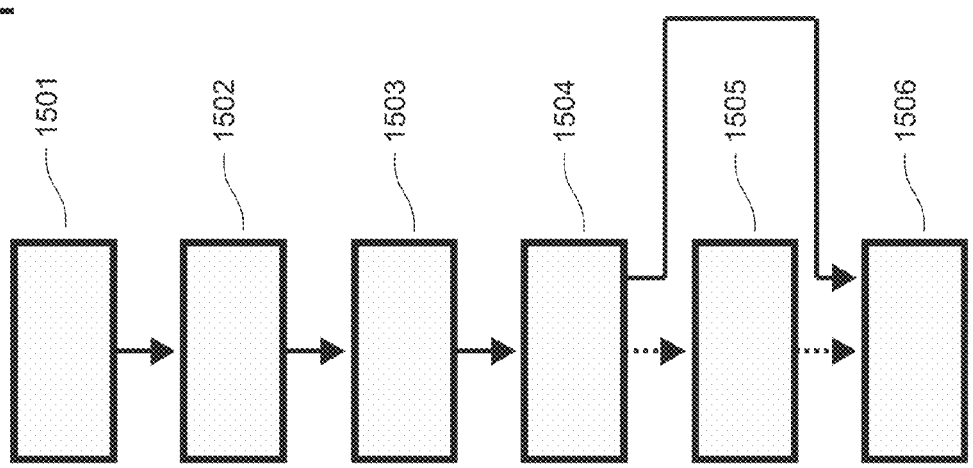

INSULATION PANEL

TECHNICAL FIELD

The present disclosure relates to construction materials made of algae and methods and plants for production thereof.

BACKGROUND

Algae are known to be used as fertilizer, as food, and as a pollution control in sewer plants. Recently, their ability to produce more biomass per unit area in a year than any other form of biomass has increased interest in algae as a renewable energy source. Cultivating algae for this purpose usually involves algae species that can produce algae oil and requires closed containers, a tightly controlled environment, and sophisticated process technology. *Chlorella*, a genus of single-celled green algae, has been used for fuel production. The presence of other algae, especially fast growing hair algae, is undesirable in such algae fuel plants.

Some algae, e.g. those of the Cladophora, have been used in fire retardant building material known in German as "Algilit". "Algilit" is known to having been used in western Siberia for many years. Algal plastics which comprise a foamed and stabilized filamentous algal fiber matrix having substantial dimensional stability are disclosed in U.S. Pat. No. 5,779,960.

Carbon dioxide is considered a green house gas, increasing concentration of which in the earth's atmosphere leads to a rise in global temperature levels, an effect often referred to as global warming. A reduction in carbon dioxide emissions is deemed desirable. Ideally, the concentration of carbon dioxide in the atmosphere would be kept constant or even reduced, by permanently withdrawing carbon dioxide from the atmosphere at the same or at a faster rate than carbon dioxide is emitted into the atmosphere. However, reducing or eliminating the emission of carbon dioxide that is generated by fossil fuel power plants such as coal, oil or gas power plants, has proven to be difficult, inefficient, and expensive. The ability to reduce carbon dioxide emissions is however of particular interest in jurisdictions that regulate carbon dioxide emissions, including taxing such emissions, for example by requiring an emitter to purchase carbon dioxide emission rights.

One approach to reducing carbon dioxide emissions from fossil fuel power plants is to pump carbon dioxide that is generated in power plants into underground storage, e.g. caverns or retired mines. However, this approach is expensive and potentially dangerous, if carbon dioxide escapes from its underground storage.

Another approach is to switch power generation plants from fossil fuels to renewable fuels, thereby reducing the dependency on coal, oil and gas as energy sources. However, renewable energy sources from crop compete with crop needed as food, are inefficient, and can at best case be carbon neutral. Burning renewable energy typically emits about the same amount of carbon dioxide that the underlying crop has withdrawn from the atmosphere during its growth. A reduction of the carbon dioxide in the atmosphere is not possible.

SUMMARY

The present disclosure reveals a new use for filamentous algae which are produced in cultivation pools filled with pre-treated waste water and into which carbon dioxide is injected to create insulating construction materials. It has been found, that dried algae mass can be used to form construction material, especially thermal and noise insulation material. The filamentous algae used in construction material bind carbon dioxide, permanently removing it from the earth's atmosphere. Construction material comprising filamentous algae is hence eligible to receive credits for carbon dioxide reductions, where such credits are legislated. The disclosed construction material comprises at least 20% of dried filamentous algae mass, but may consist of up to 100% of dried algae mass.

Suitable algae for use in construction material are filamentous species, which grow in strings of connected cells. Filamentous algae may be branching, or non-branching, and may be referred to as hair algae or string algae.

Several genera of green algae from the order Zygnematales have been found suitable for use in construction. More specifically, species from the genera of the Spirogyra, the Zygnema, and the Mougeotia, have all been found to have desirable characteristics for use in insulation material.

Other suitable algae are species from the Cladophora, a genus of reticulated filamentous green algae from the order of Cladophorales, specifically the Cladophora fracta. Species from the Ulothrix, from the order of Ulotrichales, have also been found suitable for construction use. Hydrodictyon of the family Hydrodictyaceae from the order Chlorococcales are suitable due to their usually pentagonal or hexagonal mesh that they form. Cladophorales, Ulotrichales, Oedogonium, Chlorococcales and Zygnematales are all green algae from the class of Chlorophyceae. Klebsormidium is a green algae of the class of Klebsormidiophyceae. Vaucheria, a genus of Xanthophyceae or yellow-green algae, characterized by multinucleate tubular branches lacking cross walls have also been found suitable for use in construction material.

Further usable as a filler within construction material are species from the Aulacoseira from the order of Aulacoseirales, species of the Melosira from the order of Melosirales, species from the Oscillatoria from the order of Nostocales, as well as species within the order of Tribonematales. Aulacoseirales and Melosirales belong to the class of Coscinodiscophyceae, Nostocales to the class of Cyanophyceae and Tribonematales to the class of Xanthophyceae.

The disclosed filamentous algae are relatively easy to cultivate and harvest. When dried, the resulting algae mass forms a material that has good thermal insulation characteristics. Beneficial thermal insulation properties are caused by small cavities within the algae mass. These cavities are small enough to not allow any significant convective heat transfer. Also, the disclosed algae comprise hollow cores, which act as natural insulation. The insulating characteristic of these hollow cores is similar to small cavities that can be found in the hair of polar bears or chamois, causing their fur to be insulating and allowing them to survive in very cold environment.

The species or combination of species of algae that is best used for producing insulation material depends on several environmental factors, such as for example temperature, sun intensity, and water hardness. Hence, it is desirable to analyze regional environmental factors to decide the most suitable species of algae or combination of species of algae that can be optimally grown at a given location.

The disclosed construction material made of dried algae mass is naturally self-extinguishing, in spite of a relatively high carbon content. This makes the disclosed material ideal for use in construction, where fire retardant characteristics are important.

While filamentous green algae species form the basis of the disclosed construction material, filler material may be used to fill small cavities within dried mass of filamentous green algae. Filler material may for example be amorphous silica which is added as a powder to the green algae mass. Another suitable filler material is diatom algae mass. Diatom algae may be grown jointly with the filamentous species for use in construction material. Especially diatom algae species of the Aulacoseirales and Melosirales whose cell wall comprises silicon dioxide (silica) form a desirable filler, which increases the self-extinguishing capability of the resulting construction material. By jointly growing filamentous and diatom algae, the diatom algae naturally adhere to the filamentous species, so they can easily be dried and processed with the diatom species.

Algae that are harvested from a cultivation plant must be cleaned and dried before they can be formed into construction material. Drying can be achieved simply by natural air drying, preferably leaving the wet algae mass exposed to sunlight. Alternatively, the algae mass can be convectively dried using hot air. The algae mass can also be vacuum dried or freeze-dried (lyophilized. Vacuum drying, in which the wet algae mass is heated while vapor is removed through a vacuum system, is especially beneficial, as it promotes the generation of small cavities within the dried algae mass, thereby improving its thermal insulating capability.

Dried algae mass is processed for use in various applications, such as for example to form upholstery material, insulating or noise-absorbing mats, fleece, packaging material, and textiles. Algae-based products are suitable for use in construction and automotive, among others. In some applications, dried algae mass, which forms a fibrous web, may be used directly, simply by cutting or otherwise forming it into a desirable shape.

For use in other applications the dried algae mass is further processed. Dried algae mass may be wrapped with a wrapping material, so that the dried algae mass is mechanically and chemically protected. Additionally, the dried algae mass may be coated with silicon dioxide, before being wrapped.

A composite material may be formed by combining dried algae mass with an additive, e.g. Epoxy. The consistency of dried algae material may also be affected by adding a binding agent such as potato starch or corn starch. An exemplary composite material comprises pieces of isotropic green algae, which are attached to each other by a binding agent. Gas bubbles may be injected into the composite material to increase its thermal insulation capability.

Several layers of dried algae mass may be used to form a multi-layer structure, the layers being connected to each other by a binding agent. To form a mechanically strong composite material, algae having a predominant orientation may be used in several layers. The algae in each layer are preferably arranged such, that their predominant orientation is non-parallel, and preferably approximately perpendicular to each other. An exemplary construction material comprises two layers of algae from the Zygnematales, their predominant orientation being approximately perpendicular to each other, and one layer of algae from the Chlorococcales, for example Hydrodictyon, which have a mesh-like structure.

Dried algae mass can be used to form insulation panels. The insulation panels preferably have a body made of 20% or more dried algae mass. The body is shaped to form honeycomb-shaped chambers, which are sealed by a foil that is attached to, e.g. laminated onto, the body.

Depending on the desired characteristics of the insulation panel, the honeycomb-shaped chambers may be evacuated, or may be filled with various materials. Evacuation or filling with dried algae mass produces insulation panels having good thermal insulation. Sand, gel, or other noise-absorbing filling materials may be used to provide good noise insulation (noise attenuation) characteristics.

Insulation panels may be constructed of two or more layers comprising honeycomb-shaped chambers. Each layer may be dedicated to a particular purpose. For example, the chambers in a first layer may be evacuated to provide good thermal insulation, whereas the chambers in a second layer may be filled with sand to provide good noise insulation.

Dried algae mass can further be converted into carbon fiber material through pyrolysis, creating mechanically strong carbon fibers from dried algae. Among many potential uses for pyrolytically created carbon fiber material made of algae mass is use as an additive in insulation materials to create tarnish capable of absorbing infrared radiation. Layers of pyrolyzed green algae may be combined by adding a binding agent as described with reference to non-pyrolyzed algae mass above.

Algae mass for use in construction is produced in algae cultivation plants. Algae need water, carbon dioxide ($CO_2$), light, and nutrients to grow. Those are provided in an open algae cultivation pond, which is exposed to the sun. The algae cultivation pond is filled with water suitable for growing algae, for example pre-treated waste water from a sewer plant. Pre-treated waste water has at least gone through a mechanical cleaning process, during which solid contaminants have been removed from the waste water. Carbon dioxide is injected into the algae cultivation pond through a gas inlet. The carbon dioxide may be extracted from the flue gas of a fossil fuel fired power plant, or from exhaust gas of any other fuel burning facility. Alternatively, flue gas that is rich in carbon dioxide from a fossil fuel fired power plant may directly be injected into the algae cultivation pond without prior extraction of carbon dioxide there from. A gas is considered rich in carbon dioxide, if the concentration of carbon dioxide therein is at least 0.1% by volume. This equals about three times the concentration of carbon dioxide that is naturally occurring in the atmosphere, which is approximately 0.0387% by volume. The amount of carbon dioxide that is injected into the algae cultivation pond is electronically controlled using a microcontroller and sensors. Electric conductivity of the water is measured by sensors to determine the amount of nutrients in the water. An exemplary value of the minimal amount of phosphorus (P) needed to grow algae is 10 μg P/l. For optimal growth 5-10 mg P/l are needed. The consumption of phosphorus with a full day of solar radiation is about 250-500 mg P $m^2$/day. Algae grow in the algae cultivation pond when it is exposed to sunlight, typically at a rate up to 100 times faster than other known renewable resources.

When a sufficiently thick layer of algae slick has formed in the algae cultivation pond, the algae are automatically harvested. The thickness of an algae slick floating in an algae cultivation pond is determined by sensors, which sense the amount of light transmitted through the algae slick by comparing a light intensity reading above and below the algae slick in the algae cultivation pond. If the thickness of algae slick has reached or exceeds a predetermined threshold, the algae are harvested, preferably automatically.

Several alternative concepts for harvesting algae, referred to as gravitational harvest, net harvest, rake harvest, circulation and overflow harvest and a harvesting machine are disclosed.

Algae cultivation plants employing gravitational harvest utilize an algae cultivation pond which has a sloped floor and a pivotable dam wall at its deep end. During an algae growth period the dam wall is closed, and the pond is filled with water that has a high concentration of phosphates, nitrates, and other nutrients, allowing algae to grow. To harvest algae from the algae cultivation pond its pivotable dam wall is opened, allowing the content of algae cultivation pond to flow down along the sloped floor into a lower reservoir. A grill located above the lower reservoir separates the algae mass from water, making it possible to reuse the water for a next growth cycle, while extracting the algae mass from the grill. Also, the algae mass may be allowed to dry on the grill. Subsequently algae mass may be collected from the grill, and subsequently dried, and processed into thermal insulation material or padding material. Two of more algae cultivation ponds may form a cascading set of algae cultivation ponds, wherein water and algae flow from an upper pond into a lower pond, when the pivotable dam wall of the upper pond is opened.

Algae cultivation plants based on net harvest comprise an algae cultivation pond, into which a net is lowered at the beginning of an algae growth cycle. Algae grow in the algae cultivation pond above the net. Net positioning sliders position the net in a submerged position at the bottom of the algae cultivation pond while algae are growing above the net. Algae are harvested by lifting the net positioning sliders into an upper position, allowing the net to emerge. Next, the net is pulled, conveying the algae from the cultivation pond to an adjacent collector reservoir, where the algae mass is allowed to dry on the net.

An algae cultivation plant based on circulation harvest comprises an algae cultivation pond which is surrounded by a wall. A circulation water inlet located at one end of the algae cultivation pond, and overflow rim located at the opposite end. The top of the overflow rim is the lowest point of the wall surrounding the algae cultivation pond, so that any excess water flows out of the algae cultivation pond over the overflow rim. The overflow rim comprises a sloped wall, so that the speed of water flowing over the rim successively increases until it flows over the rim. A conveyor system is located in a collector reservoir adjacent to and underneath the overflow rim. During operation, water circulates from a collector reservoir underneath the conveyor system through the circulation water inlet into the algae cultivation pond, and across the overflow rim back into the collector reservoir. Algae slick floating with the circulating water flows across the overflow rim, and lands on the conveyor system, where it is separated from the water. The algae mass is conveyed by the conveyor system to a collection location for further processing.

The algae cultivation plant based on circulation harvest can be operated in a continuous operating mode, wherein the water level in the algae cultivation pond is kept high, so that algae continuously flows across the overflow rim onto the conveyor system. The plant can also be operated in a burst mode, wherein the water level in the algae cultivation pond is kept below the overflow rim during an algae growth phase and wherein water is added to the algae cultivation pond during a harvest phase, causing algae growing in the algae cultivation pond to flow across the overflow rim and onto the conveyor system.

An algae cultivation plant based on rake harvest comprises an algae cultivation pond surround by a wall. An overflow rim located at one end of the algae cultivation pond, the top of the overflow rim being the lowest point of the wall surrounds the algae cultivation pond. A conveyor is located in a collector reservoir adjacent and underneath the overflow rim. A floating rake, which is attached to a pulley system, is used to pull algae slick growing in the algae cultivation pond across the overflow rim and onto the conveyor.

In another alternative, algae growing in an algae cultivation pond can be harvested by an algae harvesting machine, which moves across a long and narrow algae cultivation pond. As the algae harvesting machine moves across the pond, algae slick is lifted from the surface of the algae cultivation pond and conveyed for collection outside the pond. The harvesting machine uses a harvesting barrel having circumferentially and axially spaced spikes to lift the algae slick from an algae cultivation pond. A conveyor barrel, located adjacent to the harvesting barrel, transports the algae slick from the harvesting barrel to a slide. At the bottom of the slide is a conveyor belt for moving the algae slick for collection outside of the algae cultivation pond.

Algae mass produced in an algae cultivation plant can be weighed on a scale to calculate the amount of carbon dioxide that is bound in the algae mass. The amount of carbon dioxide that has been absorbed in the algae can be calculated by multiplying the dried mass of the algae mass with a multiplication factor, which is specific for each species of algae, and generally around two. The bound carbon dioxide mass may be reported to obtain tax credits, carbon emission certificates, or any other financial benefit.

The disclosed algae cultivation plants are based on a common method for producing green algae mass, which comprises several steps. A first step is to provide an algae cultivation pond filled with water in which the green algae can grow. Algae or algae spores are provided in the algae cultivation pond to start the growth of algae. The algae cultivation pond may for example comprise spikes to which a small amount of algae attach and remain attached even when algae are harvested from the algae cultivation pond. The algae attached to the spikes provide a basis for successive harvest cycles. The algae cultivation pond is filled with water and exposed to sunlight, allowing algae to grow therein. To foster algae growth carbon dioxide from an exhaust gas of a fuel burning facility is injected into the algae cultivation pond. Alternatively, carbon dioxide may be injected into water outside the algae cultivation pond, and the carbon-dioxide saturated water inserted into the algae cultivation pond. The growth of algae in the algae cultivation pond is sensed, and algae are harvested from the algae cultivation pond when a sufficiently thick layer of algae has formed. Harvested algae are dried to form a green algae mass, for example by air-drying, freeze drying, or vacuum drying.

Nutrients to facilitate algae growth may be provided by injecting pre-treated waste water into the algae cultivation pond. Algae mass may be weighed and an amount of carbon dioxide absorbed within the green algae mass may be calculated for the purpose of obtaining a financial benefit associated with reducing carbon dioxide emissions into the atmosphere, e.g. to avoid having to purchase carbon emission certificates.

The following detailed description of the invention is merely exemplary in nature and is not intended to limit the invention or the application and uses of the invention. Furthermore, there is no intention to be bound by any theory presented in the preceding background of the invention or the following detailed description of the invention.

BRIEF DESCRIPTION OF THE DRAWINGS

FIG. 5a illustrates the structure of a Spirogyra alga.
FIG. 5b shows a cross section through a Spirogyra alga.
FIG. 6a shows an algae mat.
FIG. 6b is a cross section through two algae mats.

FIG. 6c is a top view of the two algae mats of FIG. 6b.

FIG. 6d illustrates a processed algae mat.

FIG. 7a shows a schematic top view of a water net algae.

FIG. 7b is a cross section of a laminate algae mat.

FIG. 8a shows a cross section and a top view of the isotropic algae mass.

FIG. 8b shows sections of algae mass.

FIG. 8c shows an insulation material.

FIG. 9a is a top view of a honeycombed structure for an insulation mat.

FIG. 9b is a cross section of the mat of FIG. 9a.

FIG. 9c shows a magnified cross section through the mat of FIG. 9a.

FIG. 10a is a top view showing a honeycombed structure for a insulation mat.

FIG. 10b is a cross section through the mat of FIG. 10a.

FIG. 10c is a cross section trough an arrangement having two insulation mats.

FIG. 11a shows an embodiment of an insulation material.

FIG. 13 illustrates harvesting of algae in an algae cultivation pond.

FIG. 14a is a side view of a harvesting machine for algae in an algae cultivation pond.

FIG. 14b is a front view of the harvesting machine of FIG. 14a.

FIG. 15 is a block diagram showing a method for producing carbon fiber from algae mass.

DETAILED DESCRIPTION

Figure 1:
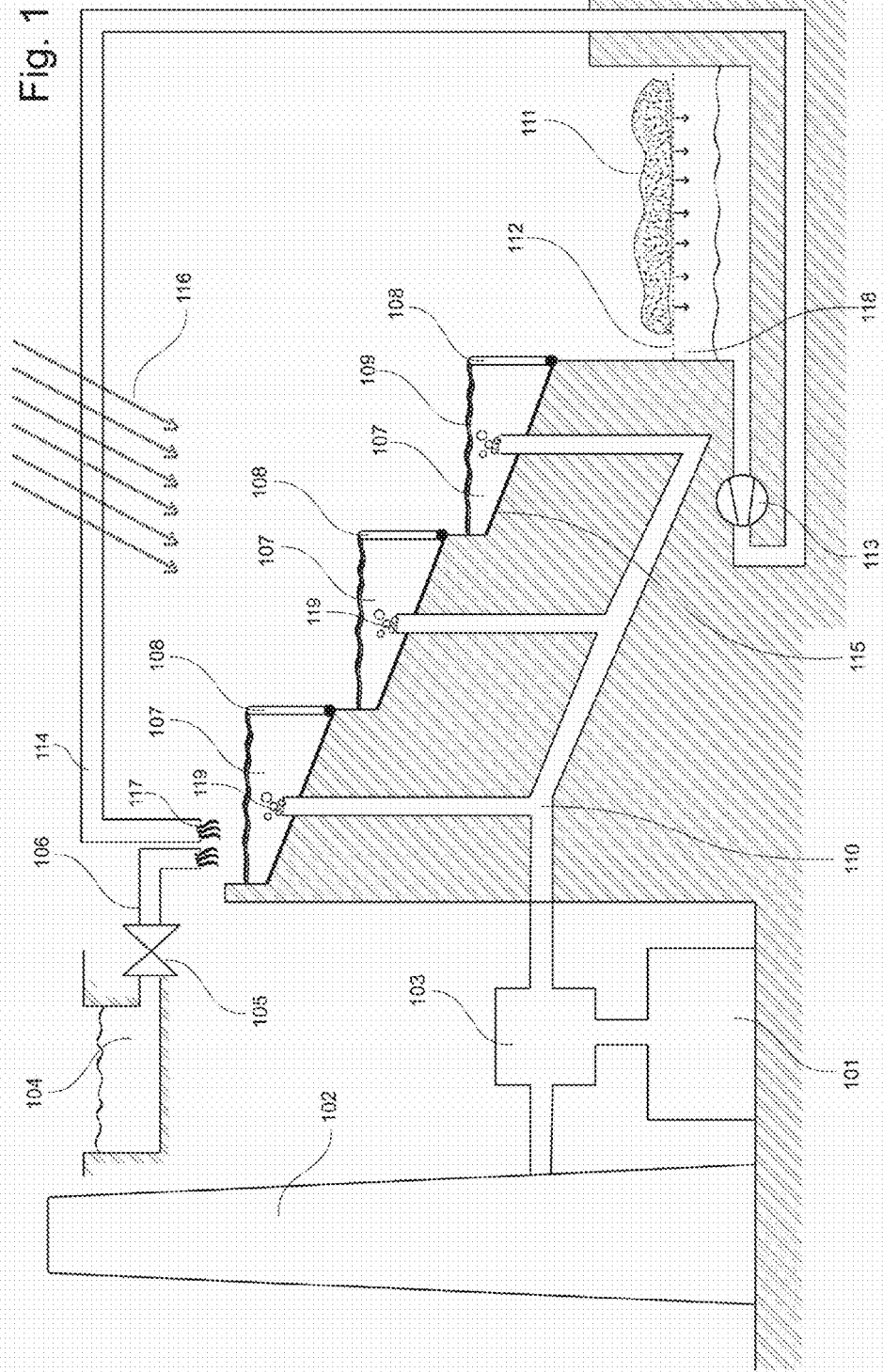
FIG. 1 shows an algae cultivation plant.

An exemplary use of filamentous algae for construction is explained with reference to Spirogyra algae, one of many filamentous algae that are suitable for use in construction, as illustrated in FIG. 5a. Spirogyra algae 500 are unbranched with cylindrical cells connected end to end in long green filaments. Cell wall 501 comprises an outer wall of cellulose and an inner wall of pectin. A ribbon shaped, serrated or scalloped, and spirally arranged chloroplast 502 is embedded within cell wall 501. Cell wall 501 further comprises nitrogen, causing spirogyra algae 500 to be self-extinguishing.

As illustrated in cross sectional view FIG. 5b a cavity 503 is formed by cell wall 501 and chloroplast 502. The average diameter 504 of Spirogyra algae 500 is approximately 30 micrometer. When dried, cavity 503 is filled with air. The small diameter 504 of the dried Spirogyra algae 500 reduces the possible convective flow of air within cavity 503, causing Spirogyra algae 500 to act as a natural heat insulator.

Diameter 504 of a Spirogyra alga is approximately 5 times larger than the diameter of artificially created carbon fibers, which have a diameter of approximately 6 micrometers. However, other than artificial fiber, the mass of the Spirogyra alga is concentrated along its outer diameter at cell wall 501, a structure that is almost impossible to artificially create. When dried, Spirogyra algae 500 have a very low density of approximately 0.06 g/cm$^3$. Dried spirogyra algae mass has a large ratio of surface area to weight, which results in high robustness for products, e.g. composite materials, made of spirogyra algae mass. The physical structure of filamentous algae is similar to that of bamboo plants, in that the plant's mass is concentrated along its outer diameter, resulting in a lightweight, but mechanically robust structure. A similar structure can be found e.g. in Spirogyra, Zygnema, Mougeotia, or Cladophora algae.

As illustrated in FIG. 6a, algae from the order Zygnematales, when dried, assume a form of a naturally fibrous algae mat 601. In calm or evenly moving water Zygnematales naturally grow in form of threads which are oriented parallel to each other. This allows algae mat 601 to be used as fleece, felt or insulation material simply by cutting or otherwise shaping it into a desired shape. Other renewable fibers, e.g. those from wood, have to be mechanically processed in energy consuming cutting processes, to achieve the same structure. The algae within algae mat 601 have a predominant orientation 602 of their cells due to anisotropic growth.

A mechanically stronger structure can be created by applying a binding agent 606 to a first algae mat 601 and a second algae mat 603 as shown in FIG. 6b. Binding agent 606 may for example be potato starch or corn starch, or any other single- or multi-component binding agent known in the art. Algae mats 601 and 603 may e.g. be soaked in a bath of binding agent. Referring to FIG. 6c algae mat 601 and algae mat 603 are then placed onto each other, such that the predominant orientation 602 of cells in algae mat 601 is about perpendicular to the predominant orientation 604 of cells in algae mat 603. As shown in FIG. 6d a two-layer algae mat 605 having a first layer of cells oriented perpendicular to a second layer of cells results. The process can be repeated to create algae mats having more than two layers.

Referring now to FIG. 7, composite material 704 utilizing different species of algae is disclosed. An exemplary composite material shown in FIG. 7b comprises three layers of algae. A center layer 701 comprises Hydrodictyon reticulatum in the family Hydrodictyaceae from the order Chlorococcales within the class of Chlorophyceae. Hydrodictyon reticulatum form a large, usually pentagonal or hexagonal, mesh which is illustrated in FIG. 7a. Outer layers 702 and 703 are dried algae from the Zygnematales, e.g. species from the genera of Spirogyra, Zygnema, Mougeotia, or Cladophora which have a fibrous, string-like, structure.

Figure 7C:
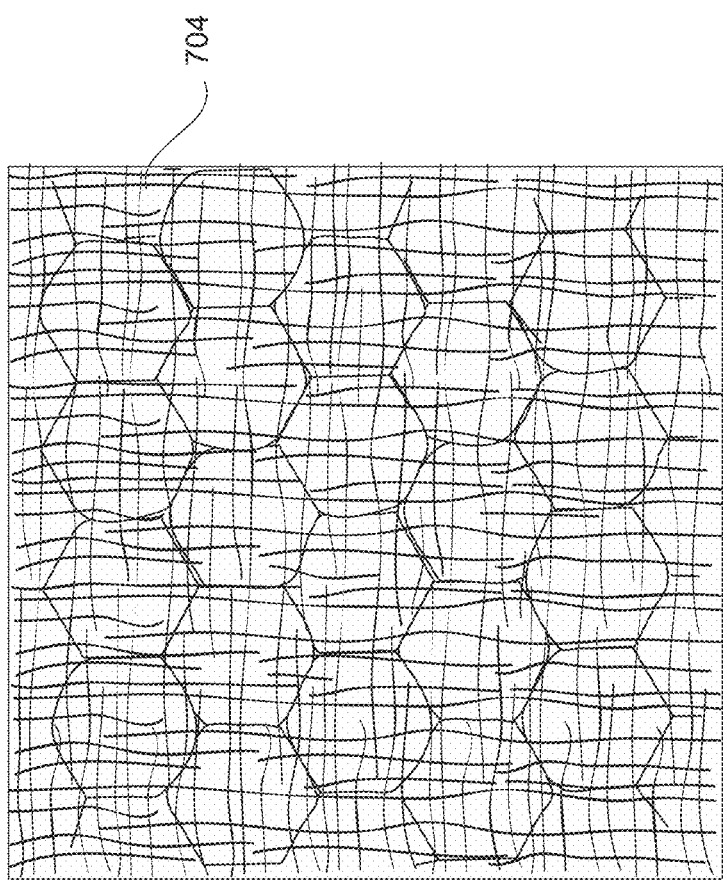
FIG. 7c is a top view of the composite material of FIG. 7b.

The composite material 704 as shown in FIG. 7c combines string-shaped algae cells in algae mats 702 and 703, and a central mesh-structure of cells in an algae mat forming central layer 701. Algae cells in mats forming outer layers 702 and 703 are oriented about perpendicular to each other. The resulting composite material 704 provides good mechanical strength and resistance against tearing. Composite material 704 comprising layers of algae mats in center layer 701 and outer layers 702 and 703 may be manufactured by adding a binding agent (not shown) to the algae mats in center layer 701, and outer layers 702 and 703. The algae mats in each layer are then placed onto each other, and pressure is applied.

Referring now to FIG. 8a, a mass 801 of isotropic dried algae is shown in a top view and a cross sectional view. As illustrated in FIG. 8b, algae mass 801 may be cut into several pieces 802. As shown in FIG. 8c, a binding agent 803 is applied to the algae pieces 802, forming a composite material 804. Composite material 804 may be processed in several ways to be used as an insulation material. Composite material 804 may e.g. be molded or pressed.

Binding agent 803 may comprise gas bubbles, e.g. carbon dioxide that has been added under pressure. During the molding or shaping of composite material 804 the gas bubbles within binding agent 803 may be allowed to expand, e.g. by reducing air pressure around the composite material 804. Alternatively, a foaming agent may be added, which generates bubbles within composite material 804. The additional bubbles in composite material 804 reduce the density of composite material 804, and increase its heat insulation performance.

Referring now to FIG. 9a, an insulation panel 911 having a honeycomb structure is shown. The walls of insulation panel 911 may be made of composite algae material or plastic. The honeycomb structure of insulation panel 911 comprises a plurality of honeycomb shaped chambers 912, which are sealed by foil 913. Depending on the intended use of insulation panel 911, chambers 912 may be filled with different materials. Chambers 912 may e.g. be filled with air or another gas for use as a heat insulation mat. Even better heat insulation may be achieved by evacuating chambers 912, which requires the algae composite material forming insulation panel 911 to be airtight.

Chambers 912 may also be filled with a filler material 914, for example loose sand or plaster for use as noise attenuator. A more detailed view of sand as filler material 914 of a chamber 912 is shown in FIG. 9b. Sand corns 915 are loosely situated within chamber 912, allowing movement of the sand corns through hollow areas 916. Noise energy is largely absorbed through mechanical friction of sand corns rubbing against each other, thereby providing good noise attenuation of the insulation panel 911. Alternatively, chambers 912 may be filled with a liquid foam, or gel containing gas bubbles, suitable to absorb energy when compressed by sound waves.

Figure 10:
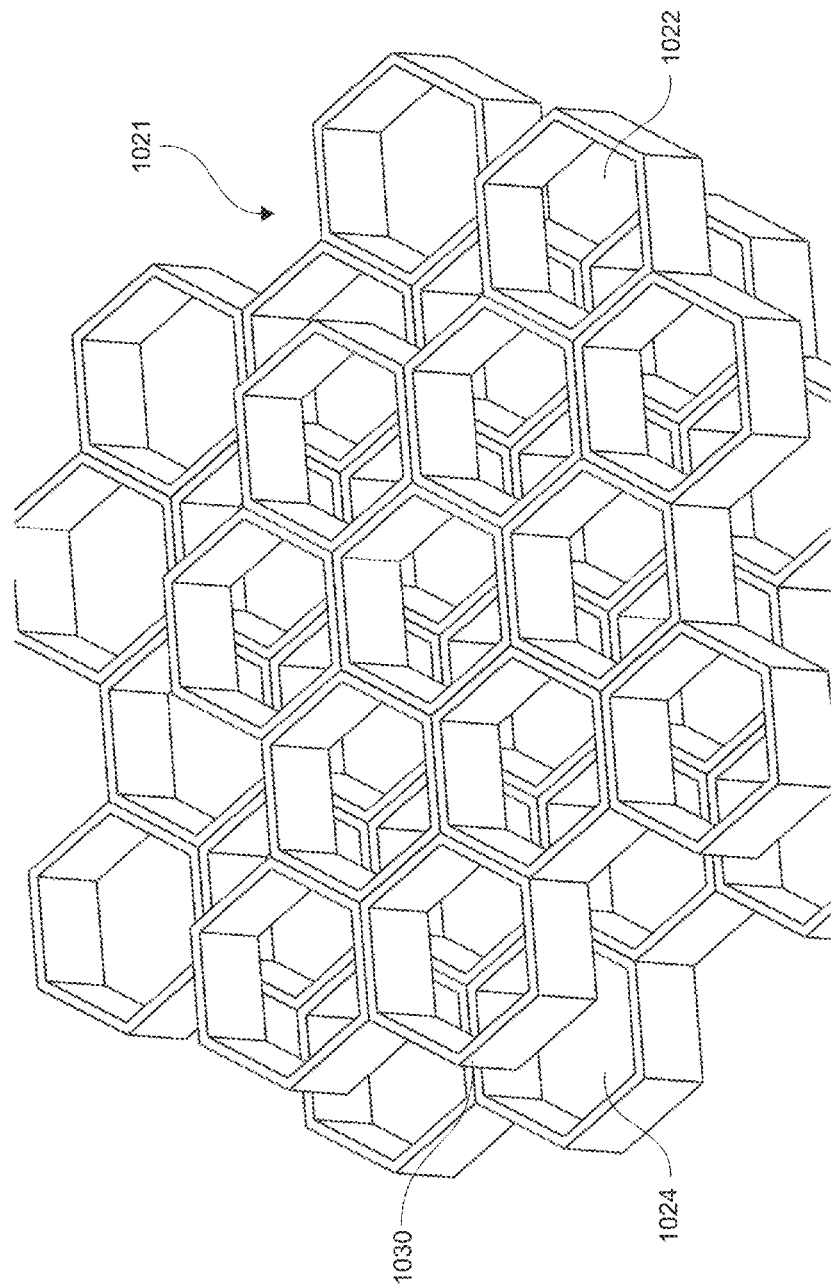

Referring to FIG. 10, an alternative structure utilizing several layers of honeycomb shaped algae mass are shown. An upper layer of honeycomb shaped algae mat 1021 comprises upper chambers 1022 and a lower layer comprises lower chambers 1024. Upper layer and lower layer only meet at small intersecting areas 1030, thereby greatly limiting the possible heat transfer between the both layers. The upper layer of algae mat 1021 is covered by top foil 1023. The lower layer of algae mat 1021 is covered by bottom foil 1025. Instead of using top foil 1023 and bottom foil 1025 algae mat 1021 may be covered by any other form of enclosing material, e.g. plasterboard or boards made of wood. Depending on the intended use upper chambers 1022 and lower chambers 1024 may be filled with the same or different material. For example, upper chambers 1022 may be filled with a noise attenuating material, while the lower chambers 1024 are filled with a heat insulating material. The noise attenuating material may e.g. be sand, gel, or any other noise attenuating material known in the art. The heat insulating material may e.g. be air, expanded algae particles, or any other heat insulating material known in the art.

An alternative structure is shown in FIG. 10c, wherein two honeycomb algae mats 1026 and 1027 such as those disclosed with reference to FIG. 9 are placed onto each other. Honeycomb algae mats 1026 and 1027 are placed in opposite orientation, such that their respective foil covers 1028 are facing outside. The honeycomb chambers of mat 1026 and 1027 are preferably displaced relative to each other by ½ of their size. Mats having different characteristics, such as a noise attenuating mat 1026 may be combined with a heat insulating mat 1027 to achieve a combined functionality of a mat that is both heat insulating and noise absorbing. While an example with two mats has been shown it should be understood that advantageous combinations utilizing more than two mats are possible.

While mats comprising dried algae mass have been found to be surprisingly beneficial, further improvements are possibly by pyrolizing algae mass to form carbon fibers. Dried spirogyra algae have a carbon content of approximately 45%. Their cell wall 501 comprises cellulose, making the algae a suitable raw material for the production of carbon fiber and carbon mats.

A method for producing carbon fiber from algae mass is illustrated in FIG. 15. In a first step 1501 algae is harvested. Next, the algae is dried in step 1502 to create dried algae mass. In the next step 1503 the dried algae mass is placed into a sealed container, wherein the algae mass is held by mounting fixtures at both ends of the sealed container. The algae mass is held under tension by the mounting fixtures. If the algae mass has a predominant orientation of its cells, it is placed into the container such that its cells are predominantly oriented parallel to the tension that is created by the mounting fixture. The predominant orientation of the tubular cells of the algae later leads to a predominant orientation of carbon fibers of carbonized algae. Next, in step 1504, the container is heated and evacuated to minimize the amount of oxygen in the container, allowing the algae mass to pyrolize. Heating of the container may occur in several steps, e.g. 600° C., 700° C., 800° C. and 900° C. Optionally, as shown in step 1505, gas created by the pyrolysis can be extracted and used as a heat source. Lastly, in step 1506, the now carbonized algae material is removed from the container.

Two carbonized algae mats can further be processed by adding a binding agent, e.g. soaking the carbonized algae mat in a binding agent, and placing them onto each other. The two mats are preferably oriented such, that the predominant orientation of carbon fibers of carbonized algae in each mat is perpendicular to each other.

Yet another example of algae-based insulation material is illustrated in FIG. 11a. As illustrated, two mats 1101 and 1104 are placed onto each other. Mats 1101 and 1104 may be algae mats having honeycomb structured chambers as disclosed with reference to FIG. 9. Mats 1101 and 1104 may also be any other suitable thermoformed or pressed material. Chambers 1103 within mat 1101 are filled with a filling material. The filling material comprises dried algae mass. Preferably, the filling material comprises dried algae mass which is mixed with silicic acid using a ratio of approximately 70% dried algae mass and 30% silicic acid. Silicic acid nanoparticles are commercially available, for example from Wacker Chemie, Munich, Germany. The filling material is held in chambers 1103 by foil 1102, which is placed onto mat 1101 in an evacuated chamber, so that air is evacuated from chambers 1103 before foil 1102 seals the chambers. The low pressure surrounding the filling material in chambers 1103 causes foil 1102 to bend concavely into chambers 1103 when mat 1101 is exposed to standard ambient air pressure.

Place onto mat 1101 is a slightly smaller mat 1104, having one fewer chamber along its diameter than mat 1101. Mat 1104 is placed onto mat 1101 with an offset, such that the center of a chamber 1103 is about one half of a chamber width offset from the center of a chamber 1106 of mat 1104. Chambers 1106 can be filled with dried algae mass, which provides good heat insulation. Chambers 1106 may also be filled with sand or gypsum, thereby providing noise attenuation. Alternatively, chambers 1106 may be filled with a mixture of dried algae mass and sand or gypsum. Filling material is added to a level which is below the side walls height, such that sealing foil 1105 can form a concave indentation above each chamber 1106. The slightly concave shape of sealing foil 1105 above each chamber 1106 guarantees, that sealing foil 1105 touches upper mat 1101 only at the vertical walls around each chamber 1106 of lower mat 1104. The limited contact of sealing foil 1105 with upper mat 1101 reduces thermal conductivity through the insulation panel 1100.

Upper mat 1101 and lower mat 1104 are enclosed by an air sealed container which forms the out wall of insulation panel 1100. A lower container tub 1107 is sealed by a container lid 1108. Insulation panel 1100 may be evacuated, removing air between the walls of container 1107, 1108 and the upper mat 1101 and lower mat 1104. Container tub 1107 and lid 1108 can be made of metalized synthetic foils. Two or more identical insulation panels 1100 may be placed adjacent to each other, every other panel being placed upside down, so that the wider upper mat 1101 of a first panel extends over top of the smaller lower mat 1104 of an adjacent panel, forming a half lap joint between both panels.

To form larger units, insulation panels 1100 can be mounted onto a supporting board 1112, for example a drywall or plasterboard.

Figure 11B:
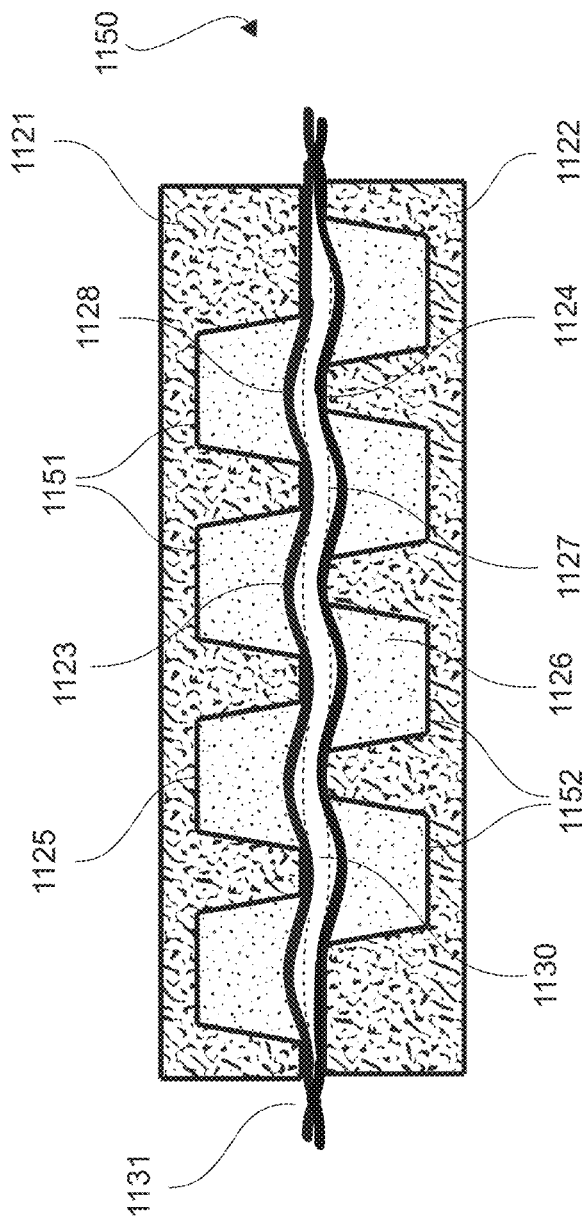
FIG. 11b shows an alternative embodiment of an insulation material.

In another example, as illustrated in FIG. 11*b*, an insulation panel 1150 is provided. Insulation panel 1150 comprises two panel members, an upper panel member 1121 and a lower panel member 1122. Each panel member 1121 and 1122 is preferably made of dried algae mass and a binder additive, e.g. gypsum. Panel members 1121 and 1122 comprise wedge shaped chambers 1151, 1152. The surface area of wedge shaped chambers 1151, 1152 may optionally be treated, e.g. by applying a metallization layer made of aluminum.

Depending on the intended application of insulation panel 1150, chambers 1151 and 1152 are filled with different filling materials. As shown, the chambers 1151 of upper panel 1121 are filled with dried algae mass being filling material 1125. The chambers 1152 of lower panel 1122 are filled with a mixture of dried algae mass and an additive, for example sand, gypsum powder, nanomaterial, silicic acid, or dried diatom algae, etc.

Chambers 1151 of upper panel member 1121 are sealed with foil 1123. Preferably, air is evacuated from the upper chamber 1151 before foil 1123 is applied, so that the air pressure in chambers 1151 is about 30 mbar. Correspondingly chambers 1152 of lower panel member 1122 are sealed by foil 1124. The low air pressure within chambers 1151 and 1152 reduced convective heat transport through panel 1150, thereby improving its heat insulation capability. When exposed to ambient air pressure of typically 1013 mbar foils 1123 and 1124 are pushed into chambers 1151, 1152, forming a characteristic concave shape above each chamber. Upper panel member 1121 and lower panel member 1122 are placed onto each other, so that chambers 1151 and chambers 1152 face each other and are displaced against each other with an offset of approximately ½ chamber width.

Upper panel member 1121 and lower panel member 1122 may be assembled in a low atmospheric pressure environment of e.g. 100 mbar. In this example an external seal 1131 around the panel between upper foil 1123 and lower foil 1124 is created. This causes only a small relative pressure difference between air in the chambers 1151, 1152 of about 30 mbar and air between upper panel member 1121 and lower panel member 1122 of about 100 mbar. Consequently, the concave indentation of upper foil 1123 and lower foil 1124 is less pronounced, as is illustrated in broken line 1127 and 1128. This gives the filling material 1125 and 1126 within chambers 1151 and 1152 some room to move within the chambers. The ability of filling material 1126 to move within chamber 1152 is desirable to provide noise attenuation. Noise energy can be absorbed by small relative movement of the dried algae mixture with sand or gypsum being filling material 1126. The material can be tuned to optimize noise absorption in a particular audio frequency by variation of pressure within chambers 1152 and the pressure between upper panel member 1121 and lower panel member 1122. Upper panel member 1121 and lower panel member 1122 only contact each other at surround seal 1131 of upper foil 1123 and lower foil 1124. The reduced contact surface between upper panel member 1121 and lower panel member 1122 provides good thermal and noise insulation.

Luckily, green algae that are suitable for use in insulation material are relatively easy to grow. Several alternative algae cultivation plants, as well as harvesting methods and machines are disclosed, which can produce green algae for use in insulation material as described above. As part of the carbon cycle green algae absorb carbon dioxide and water under sunlight to produce carbohydrate energy, leaving oxygen as a byproduct. Hence it is desirable to combine algae cultivation plants with fossil fuel burning facilities, for example power plants or other industrial facilities that generate carbon dioxide. The algae cultivation plant in such a combination absorbs some of all of the carbon dioxide that is generated by the power plant or industrial facility, thereby reducing the carbon dioxide emissions. The ability to reduce carbon dioxide emissions is of particular interest in jurisdictions that regulate carbon dioxide emissions, possibly taxing such emissions, for example by requiring an emitter to purchase carbon dioxide emission rights.

Referring to FIG. 1, a diagram of an exemplary algae cultivation plant in combination with a carbon dioxide generating facility is illustrated generally. The exemplary plant includes a cascading set of algae cultivation ponds 107 having sloped floors 115. The ponds are filled with water that is rich in phosphates, nitrates, and other nutrients. More specifically, the ponds may be filled with pre-treated waste water 104 from a sewer plant or another source. Water in algae cultivation ponds 107 circulates trough circulation pump 113. The water in ponds 107 is rich in nutrients for cultivating algae and contains algae spores.

Carbon dioxide from a fuel burning power plant is extracted from the power plant's flue gas. The fuel burning power plant may for example be a fossil fuel burning power plant such as a gar or coal power plant. The fuel burning power plant may also be a biogas burning power plant. A carbon dioxide extractor and distributor 103 extracts carbon dioxide from the power plant's flue 102 and pumps carbon dioxide into carbon dioxide storage tank 101, gas inlet pipes 110, or both. Carbon dioxide storage tank 101 is used to store carbon dioxide for use during downtimes when the power plant is not operating. Carbon dioxide from either the flue 102 or carbon dioxide storage tank 101 is pumped through extractor and distributor 103 and injected into algae cultivation ponds 107 through gas inlet pipes 110. Alternatively, the step of extracting carbon dioxide from the flue gas may be omitted, and flue gas that is rich in carbon dioxide may directly be pumped from flue 102 into carbon dioxide storage tank 101 or gas inlet pipes 110 for injection into algae cultivation ponds 107. A gas is considered rich in carbon dioxide, if the concentration of carbon dioxide therein is at least 0.1% by volume. This equals about three times the concentration of carbon dioxide that is naturally occurring in the atmosphere, which is approximately 0.0387% by volume.

The amount of carbon dioxide or flue gas that is injected into algae cultivation ponds 107 is controlled by a control system based on several inputs. Among the inputs of the control system are one or more of the water level in ponds 107, temperature of the water in ponds 107, acidity of the water in ponds 107, intensity of sunlight 116, and sunlight intensity in pond 107 below algae slick 109, to create optimal growth conditions for algae in ponds 107.

The control system may further comprise sensors for sensing air pressure and water pressure in the algae cultivation ponds 107 and control the pressure of carbon dioxide or flue gas in gas inlet pipes 110 to be below the sum of air and water pressure, thereby avoiding excess carbon dioxide or flue gas to escape through algae cultivation ponds 107.

The control system comprises tables stored in electronic memory, correlating sensors inputs for sunlight intensity, water oxygen saturation and water acidity in ponds 107 with an optimal carbon dioxide or flue gas injection rate. For example, the amount of carbon dioxide injected into pond 107 increases with increasing sunlight intensity and decreases with decreasing sunlight intensity. The data in the tables may be empirically derived trough tests and be specific for different kinds of algae. The control system controls the amount of carbon dioxide or flue gas injected into the algae cultivation ponds 107, and the amount of waste water 104 inserted through waste water valve 105 and waste water inlet 106. The control system further controls the amount of water 117 that is recycled through from collector basin 118 through circulation inlet 114 into algae cultivation pond 107.

Continuous growth of algae in algae cultivation ponds 107 leads to formation of an algae slick 109, which floats on top of the water in algae cultivation pond 107 and prevents sunlight from penetrating the water, thereby reducing further growth of algae in algae cultivation pond 107. Sensors (not illustrated) determine the thickness of algae slick 109 and generate a signal, once a predetermined thickness has been reached. Responsive to the signal, the injection of carbon dioxide or flue gas into algae cultivation pond 107 is stopped, and gravitational harvest of the algae is initiated. Thickness of the algae slick 109 may be determined by comparing sunlight intensity measured by a first sensor outside the algae cultivation pond 107 with sunlight intensity measured by a second sensor within the algae cultivation pond 107. The second sensor is located within the algae cultivation pond 107 below the algae slick 109. A large difference in sunlight intensity between the first and the second sensor indicates a thick, light absorbing algae slick 109. Instead of utilizing sunlight, an artificial light source (not shown) may be used to determine the thickness of algae slick 109.

A carbon dioxide sensor may be located above the water level of algae cultivation pond 107 to reduce or stop the injection of carbon dioxide or flue gas into algae cultivation pond 107, if increased levels of carbon dioxide are measured to be escaping algae cultivation pond 107.

Algae cultivation ponds 107 comprise a sloped floor 115 and a pivotable dam wall 108. Algae are harvested by opening pivotable dam walls 108, which pivot in a downhill direction, allowing water and algae slick 109 to flow downhill from algae cultivation ponds 107 into a collector basin 118. Grill 112 is used to separate algae mass 111 from the water. As water and algae slick 109 from ponds 107 slides downhill the sloped floor 115 of ponds 107 into collector basin 118 algae mass 111 is caught on grill 112, while water 117 flows through grill 112 into collector basin 118. Algae mass 111 may be left on grill 112 to dry, and be removed from grill 112 for further processing.

Water 117 may be recycled by pumping water 117 from collector basin 118 through circulation pump 113 and circulation inlet 114 back into pond 107.

If flue gas from flue 102 is directly injected into ponds 107, it beneficially heats the water in ponds 107, thereby causing optimal conditions for algae growth.

An aerator device 119 may be operatively connected to the outlet of carbon dioxide carrying gas inlet pipe 110 into ponds 107. Aerator device 119, which may be a membrane comprising small holes, causes carbon dioxide or flue gas from gas inlet pipe 110 to form small bubbles when injected into pond 107. These bubbles support a uniform saturation of pond 107 with carbon dioxide. They further spread sunlight entering pond 107, causing an increases photosynthesis activity of the algae growing in pond 107.

Opening and closing pivotable dam walls 108 causes alternating growth and harvesting cycles, wherein the pivotable dam walls 108 are closed and ponds 107 are filled with water during a growth cycle and pivotable dam walls 108 are opened during a harvesting cycle.

Algae mass 111 that has been removed from grill 112 may be dried and processes into construction material as described above. Algae mass 111 may also be utilized as a resource for pharmaceutical, medical or cosmetic use. Algae mass 111 may further be used as a resource for animal food, renewable fuel, fertilizer, or natural fiber construction material.

Figure 2:
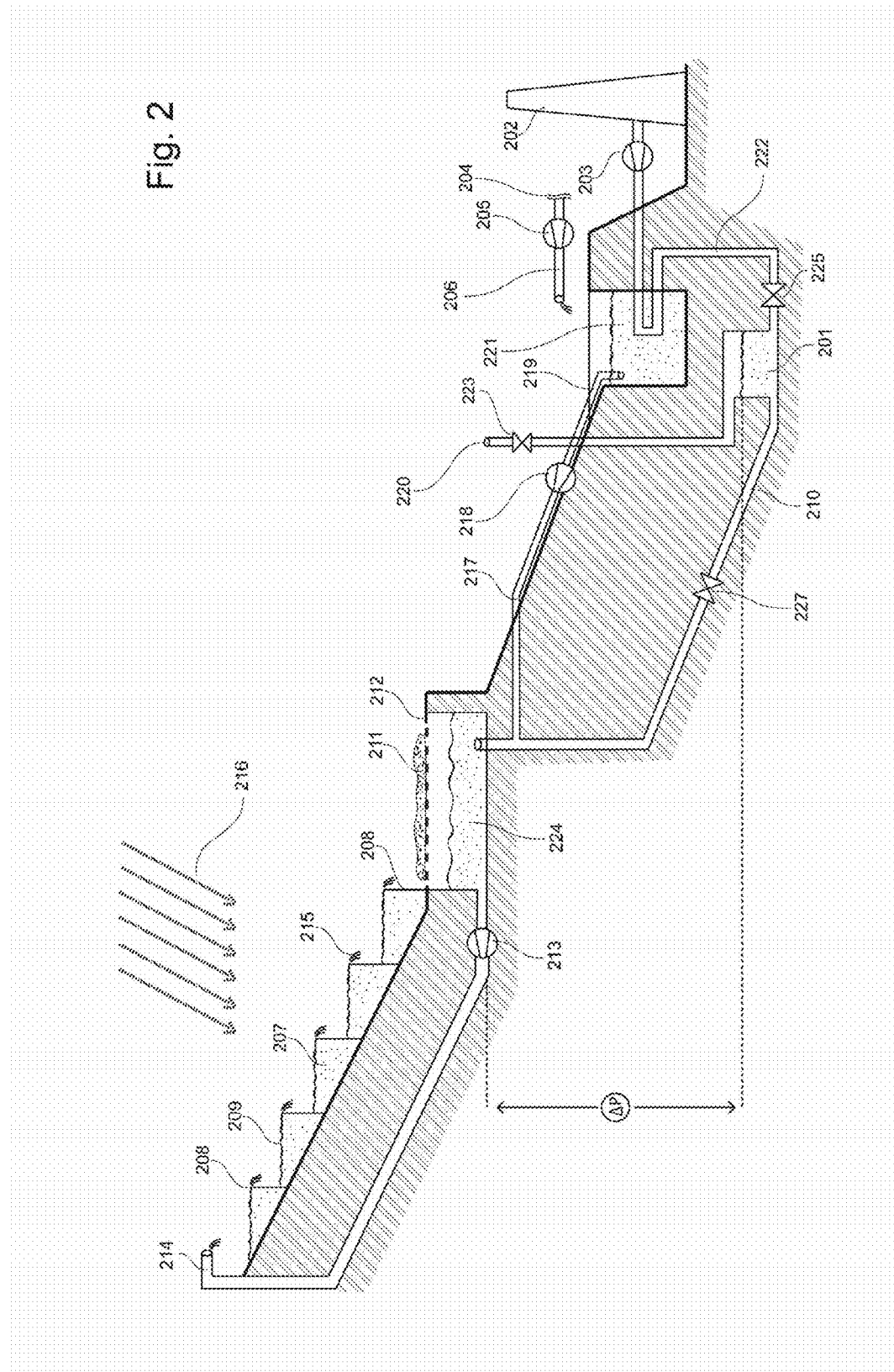
FIG. 2 is a schematic illustration of an algae cultivation plant showing additional details.

An alternative algae cultivation plant using an indirect injection of carbon dioxide is disclosed with reference to FIG. 2. Several algae cultivation ponds 207 are provided, arranged in a cascade along the slope of a hill or mountain, each having a wall 208 that can be lowered. Below the last cultivation pond 207 is an overflow and mixing reservoir, which is adapted to inject carbon dioxide and nutrients for algae cultivation thereto. Water circulates from circulation inlet 214 into the uppermost cultivation pond 207, through the cascading set of cultivation ponds 207, and the overflow and mixing reservoir 224. The circulation is facilitated by circulation pump 213, which pumps water from the overflow and mixing reservoir 224 uphill to circulation inlet 214 and the uppermost cultivation pond 207.

To grow, algae need water, nutrients, carbon dioxide, and sunlight. The open structure of algae cultivation ponds 207 exposes algae to sunlight 216. Alternatively algae cultivation pond 207 may be underneath a transparent cover through which sunlight can enter the algae cultivation pond 207. The sunlight exposure may be amplified by placing reflective material onto the floor of algae cultivation ponds 207, thereby exposing algae not only to the direct sunlight 216, but also to light that is reflected of the floor of algae cultivation ponds 207. Alternatively, algae cultivation ponds 207 may be made of a reflective material, e.g. stainless steel or alloy to achieve the same effect.

Nutrients are added to the water in cultivation ponds 207 through overflow and mixing reservoir 224. Nutrients may specifically include phosphates and nitrates, which can be a side product of sewer plants. Water that is rich in nutrients is pumped through pipe 204 and pump 205 and inlet 206 into a heating reservoir 221. Pump 218 has an inlet pipe 219 which reaches into heating reservoir 221. Pump 218 pumps warm, nutrient rich water from heating reservoir 221 through outlet pipe 217 into overflow and mixing reservoir 224, where it enters the water circulation through cultivation ponds 207.

The necessary carbon dioxide to stimulate growth of algae in algae cultivation ponds 207 stems from a powerplant or other facility producing gas that is rich in carbon dioxide. Carbon dioxide rich gas is diverted from flue 202 to compressor 203, where the gas is compressed to about 6.5 bar. Through gas pipe 222 the warm, carbon dioxide rich gas is pumped through a heat exchanger in heating reservoir 221, thereby cooling the gas in gas pipe 222 and heating the nutrient rich water in heating reservoir 221. Through a control valve 225, which also acts as a check valve, the carbon dioxide rich gas is injected into an underground water reservoir 201. Underground water reservoir 201 is a sealed pressure container. Overflow and mixing reservoir 224 and underground water reservoir 201 are connected by pipe 210. Underground water reservoir 201 is located lower than the open overflow and mixing reservoir 224, for example 60 meters below the overflow and mixing reservoir 224. Consequently, the pressure in underground water reservoir 201 is approximately ΔP=6 bar above the pressure at the bottom of overflow and mixing reservoir 224.

Water within the underground water reservoir 201 having a temperature of 10° C. and a pressure of 6 bar can absorb 6 gram of carbon dioxide per liter. Underground water reservoir 201 can therefore store carbon dioxide, for example carbon dioxide that is generated at night, when due to lack of sunlight the algae in cultivation ponds 207 can't grow, and hence don't need any carbon dioxide. An underground reservoir holding a volume of 1000 m³ of water at 10° C. and 6 bar can store 6000 kg of $CO_2$. Rest gas having low $CO_2$ content can escape the underground water reservoir 201 through pressure relieve valve 223 in pipe 220. Flowing in opposite direction, pipe 220 may also be used to add water into underground water reservoir 201.

Assuming a temperature of 22° C. and standard atmospheric pressure of 1 bar, water in overflow and mixing reservoir 224 can store only 1.5 gram of carbon dioxide per liter. Therefore, carbon dioxide rich water from underground water reservoir 201 is added to overflow and mixing reservoir 224 through control valve 227 at a maximum ration of 1 liter of water from underground water reservoir 201 per every 3 liter of water in overflow and mixing reservoir 224. Carbon dioxide mixed into the water of overflow and mixing reservoir 224 enters the circulation through the cultivation ponds 207, where the carbon dioxide is absorbed by the growing algae.

Algae from the order Zygnematales, especially species from the genera of the Spirogyra, the Zygnema, and the Mougeotia, and Hydrodictyon algae from the order Chlorococcales grow close to the surface of cultivation ponds 207, forming algae slick 209. Sunlight 216 is used for the photosynthesis of algae slick 209, absorbing primarily blue and red, including near infrared, light. Zygnema and Spirogyra algae grow in a preferred orientation of their cells.

To harvest algae from cultivation ponds 207, the lower walls 208 of algae cultivation ponds 207 be lowered, so that water and algae contained in the cultivation ponds flows downhill towards overflow and mixing reservoir 224. A grill 212 is provided above overflow and mixing reservoir 224 to capture algae mass 211 and separate it from water of the cultivation ponds 207. Algae mass 211 may be left on grill 212 to air dry, or removed when still wet for further processing.

Figure 3:
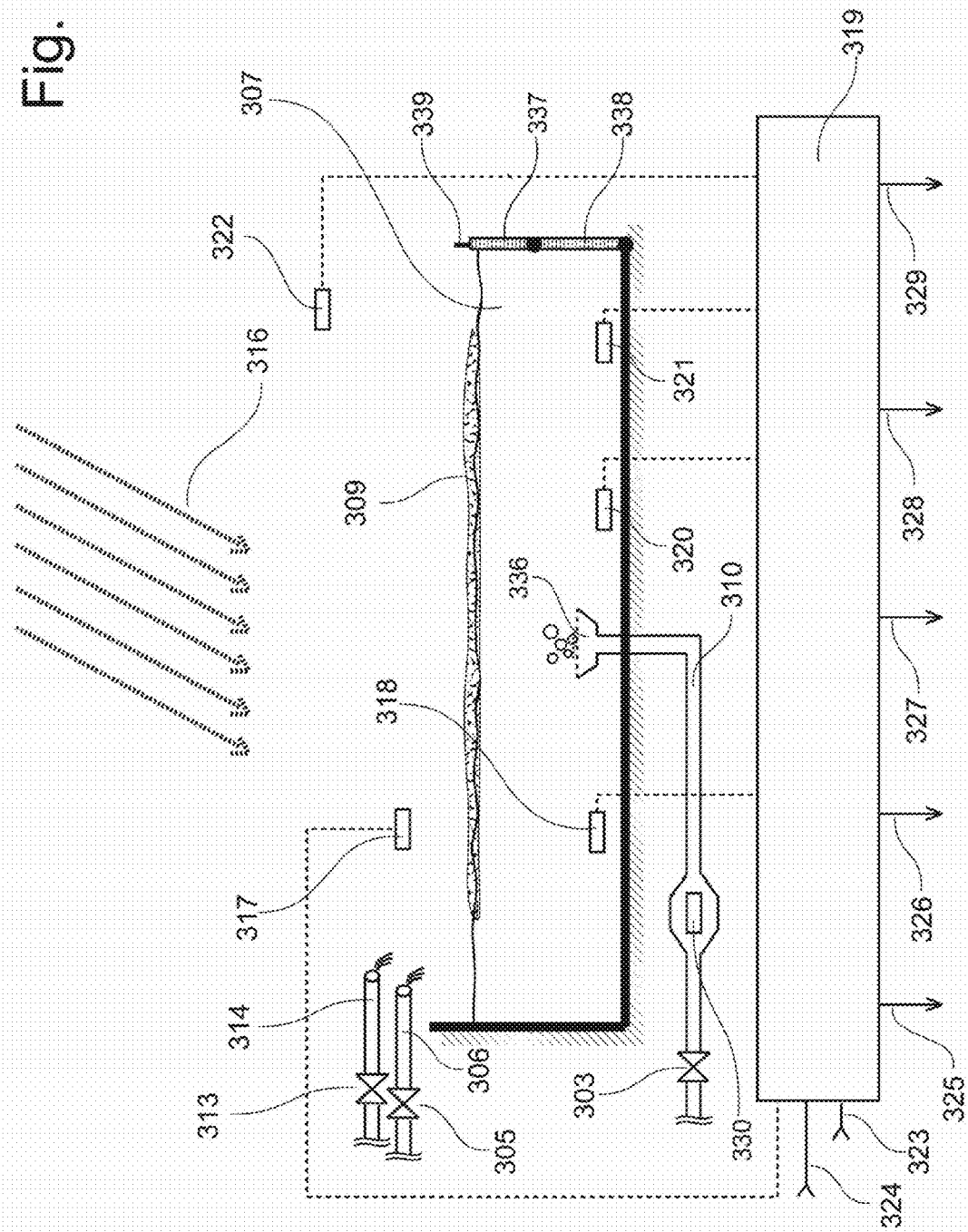
FIG. 3 illustrates a measurement and control device for algae cultivation in an open growth facility.

The right time to harvest algae can be determined by a control system as illustrated in FIG. 3. Algae 309 grow in an algae cultivation pond 307, which is filled with water that is rich in nutrients and carbon dioxide. Algae 309 hereby forms an algae slick which floats on the water of algae cultivation pond 307. A side wall 338 having a pivotable wall segment 337 is provided. An overflow gate 339 extends above pivotable wall segment 337, allowing excess water to flow through it, while holding algae 309 back inside algae cultivation pond 307.

Through valve 305 and first inlet 306 an aqueous nutrient solution can be added to algae cultivation pond 307. The aqueous nutrient solution may for example we water that is rich in phosphates and nitrates, a typical byproduct of sewer plants.

Through valve 313 and second inlet 314 fresh water and algae spores can be added to algae cultivation pond 307. Second inlet 314 may also be connected to a circulation pump to circulate water in algae cultivation pond 307.

An aerator 336 is provided, through which a gas, e.g. carbon dioxide, flue gas, air, or a mixture thereof, can be injected into algae cultivation pond 307. The amount of gas is controlled through gas inlet valve 303. The volume or mass flow of gas through gas inlet pipe 310 into aerator 336 is measured by a volume flow or mass flow sensor 330.

Algae 309 grow in the presence of sunlight 316. The intensity of sunlight 316 is measured by exterior sunlight sensor 317, which is mounted outside of algae cultivation pond 307. A second, submersed light sensor 318 is disposed inside algae cultivation pond 307, located under algae 309 that are floating in algae cultivation pond 307. Both exterior sunlight sensor 317 and submersed light sensor 318 are operatively connected to a central control unit 319. Central control unit 319 is adapted to read data from exterior sunlight sensor 317 and submersed light sensor 318. By comparing data from exterior sunlight sensor 317 and submersed light sensor 318 underneath algae 309, the thickness of algae 309 can be determined. A thicker layer of algae 309 absorbs more light, thereby leading to a larger difference in light sensed between exterior sunlight sensor 317 and submersed light sensor 318. The difference in sensor measurements between exterior sunlight sensor 317 and submersed light sensor 318 is used as an input to an algorithm in central control unit 319 which determined the right time to harvest algae 309. A more accurate measurement may be achieved by using an artificial light source (not shown) to illuminate submersed light sensor 318 trough algae 309 with a predetermined light intensity.

While exterior sunlight sensor 317 and submersed light sensor 318 are used to determine sufficient thickness of algae 309 for harvest, information from one or both of these sensors is also used to determine the correct amount of carbon dioxide to inject through aerator 336 into algae cultivation pond 307. The amount of carbon dioxide that can be processed by photosynthesis in algae 309 depends on the amount of sunlight 316, and changes over the course of a day. At night, exterior sunlight sensor 317 detects the absence of sunlight 316. Central control unit 319, responsive to a signal from exterior sunlight sensor 317 indicating darkness, closes gas inlet valve 303 through its output 327.

Central control unit 319 is an industrial control system, such as a programmable logic controller. Central control unit 319 comprises a microcontroller, power supply, electronic memory, and input and output circuitry such as for example A/D converters, D/A converters, and PWM signal generators. Central control unit 319 is powered through power input 324.

Central control unit 319 also determines and control optimal growth conditions for algae 309. Operatively connected to central control unit 319 is further a temperature sensor 320, configured to measure the temperature of water inside algae cultivation pond 307. A pH probe 321 is also operatively connected to central control unit 319 and adapted to measure the acidity of water in algae cultivation pond 307.

An external $CO_2$ sensor 322 is provided outside algae cultivation pond 307, positioned such that it can sense carbon dioxide concentration around algae cultivation pond 307, the $CO_2$ sensor 322 being operatively connected to central control unit 319. If elevated carbon dioxide levels are sensed by $CO_2$ sensor 322, central control unit 319 reduces the inflow of carbon dioxide into algae cultivation pond 307 through aerator 336 by closing gas inlet valve 303. Potentially dangerous levels of $CO_2$ sensed by $CO_2$ sensor 322 can trigger an visual or audible alarm, alerting personnel of a potential health risk around algae cultivation pond 307.

Outputs 325 through 329 of central control unit 319 are connected to the various actuators of the system. More specifically, output 325 is operatively connected to valve 305, providing central control unit 319 control over the inflow of nutrients into algae cultivation pond 307. Output 326 is operatively connected to valve 313, providing central control unit 319 control over the inflow of fresh water, or water circulation into algae cultivation pond 307. Output 327 is operatively connected to gas inlet valve 303, providing central control unit 319 control over the flow of carbon dioxide into algae cultivation pond 307. Output 328 is operatively connected to pivotable wall segment 337, allowing central control unit 319 to open algae cultivation pond 307 so that algae and water flow out. Lastly, output 329 provides a diagnostic interface for use with a diagnostic control device (not shown).

An external input 323 is used to program central control unit 319. The external input may e.g. be a connection to a computer system for downloading tables of empirically gathered data that correlate sensor data from one or more of sensors which are operatively connected to central control unit 319 with a suitable carbon dioxide volume flow. Central control unit 319 in this example controls gas inlet valve 303, using feedback from mass flow sensor 330, to achieve a predetermined flow of carbon dioxide through aerator 336 into algae cultivation pond 307. The target value of carbon dioxide flow is determined through one or more lookup tables, which correlate sensor inputs with a target volume flow of carbon dioxide.

Alternatively, external input 323 may provide a pH setpoint. In this example central control unit 319 controls the acidity water inside algae cultivation pond 307. For some green algae, the water acidity, measured by pH probe 321, is kept preferably between pH 6.0 and 9.2. A max acidity of pH 10.0 should not be exceeded to prevent damage to the algae in algae cultivation pond 307. The acidity of water in algae cultivation pond 307 is controlled by increasing or decreasing the amount of carbon dioxide that enters algae cultivation pond 307 through gas inlet valve 303. If the water in algae cultivation pond becomes too acidic, central control unit 319 adds fresh water by controlling valve 313.

Central control unit 319 may be connected to additional sensors, e.g. an atmospheric pressure sensor, or a water pressure sensor (not shown). Central control unit 319 may comprise programmable operating parameters, e.g. water hardness of water in algae cultivation pond 307, which can be determined through manual tests and entered manually into central control unit 319.

Central control unit 319 is configured to create optimal growth conditions for a particular species of algae to be grown in algae cultivation pond 307. Algae species from the genera of the Spirogyra, for example, thrive in water having a temperature of 25° Celsius, and a pH-value of between 6.2 and 8.2, preferably 7.2. The ideal acidity of water to foster growth of Spirogyra algae depends on its hardness, as illustrated in the table below:

| Carbonate hardness | pH value |
| --- | --- |
| 7 | 6.8 |
| 11 | 7.0 |
| 14 | 7.1 |

Central control unit 319 is configured to regulate acidity of the water to a predetermined target level, which is configured for each installation of an algae cultivation pond based on the hardness of water to be used in the algae cultivation pond.

Figure 4:
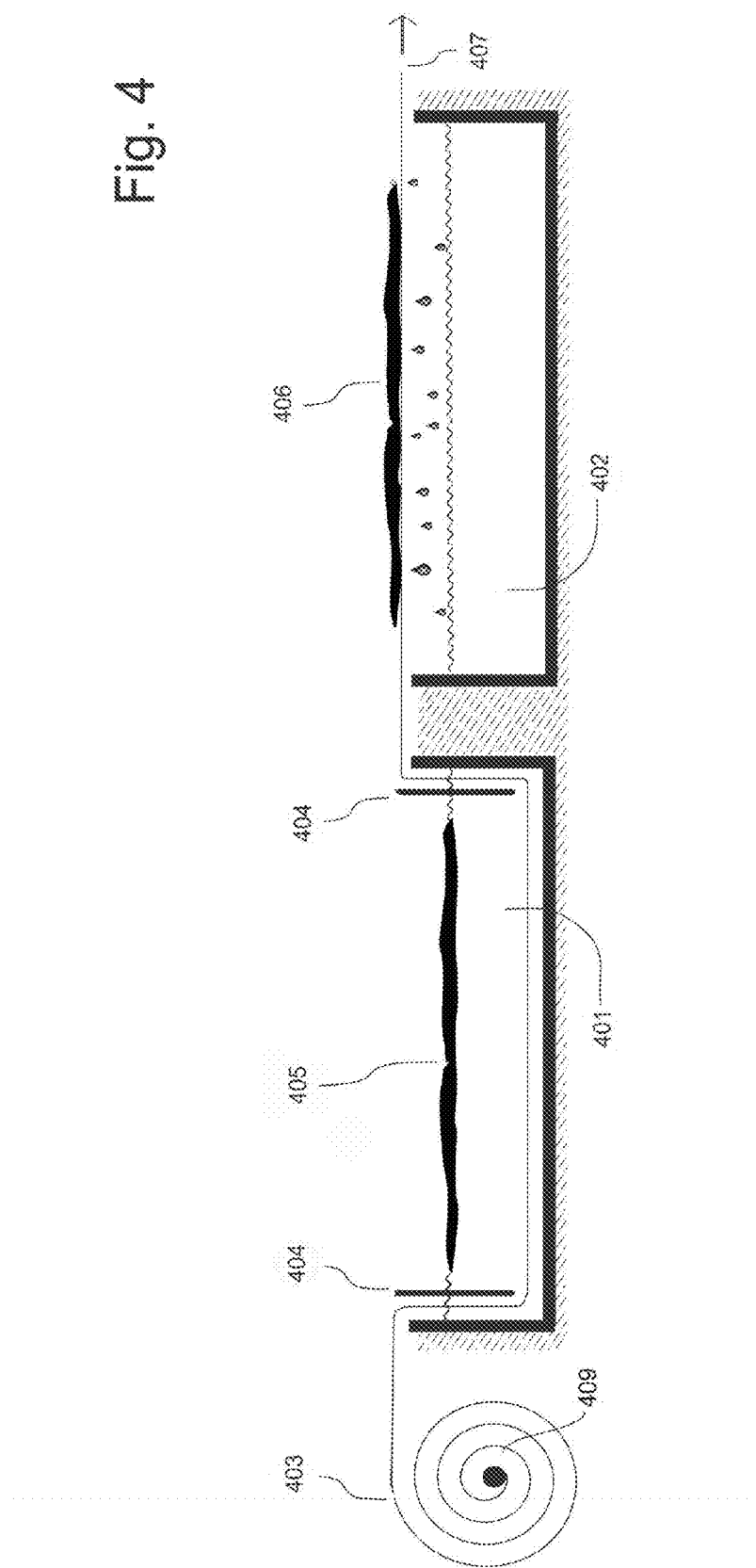
FIG. 4 shows an algae cultivation plant suitable for use in even terrain utilizing meshwork harvesting.

Referring now to FIG. 4, an alternative design for cultivating and processing algae using net harvest is illustrated. The algae cultivation ponds shown in FIG. 1, FIG. 2 and FIG. 3 utilize gravitational harvest, in which algae is harvested by opening an algae cultivation pond, allowing its content to flow down a slope through a harvesting grill. In contrast, the design illustrated in FIG. 4 does not need a sloped arrangement of algae cultivation ponds, and leans itself for use in flat terrain.

An algae cultivation pond 401 is provided, which is located adjacent to a collector reservoir 402 of similar size. A net 403 is provided, the width of which extends across algae cultivation pond 401. Net 403 is rolled into a roll 409, which is located at one end of algae cultivation pond 401. Net 403 extends along algae cultivation pond 401 and collector reservoir 402. Net 403 is connected to a pulling device 407 located at the opposite end of collector reservoir 402. Net positioning sliders 404 are provided, through which net 403 can be pushed to the bottom of algae cultivation pond 401 or collector reservoir 402. FIG. 4 shows net 403 being positioned at the bottom of algae cultivation pond 401 by net positioning sliders 404, which are in their lowered position.

Algae cultivation pond 401 uses the water circulation, carbon dioxide injection, and control concepts described with reference to FIG. 1, FIG. 2 and FIG. 3 above. For simplicity, those are not shown in FIG. 4.

To cultivate algae, net 403 is lowered towards the bottom of algae cultivation pond 401 by lowering net positioning sliders 404. This is done before any algae are allowed to grow in algae cultivation pond 401. Algae are then allowed to grow in algae cultivation pond 401 by injecting algae spores, carbon dioxide, and nutrients are described. Once algae 405 have grown sufficiently thick, they are harvested.

To harvest algae 405, net positioning sliders 404 are lifted into their upper position, which is above the water level of water in algae cultivation pond 401. Pulling device 407 is activated, thereby lifting net 403 out of algae cultivation pond 401, conveying algae 405 into position of algae mass 406. Algae mass 406 is left in position above collector reservoir 402 to dry.

Depending on the application, dried algae mass 406 is removed from net 403 for further processing. Alternatively, algae mass 406 may be processed jointly with net 403, which becomes part of a raw material. The process of growing and harvesting algae can continue, until net 403 on roll 409 is exhausted. Alternatively, net 403 may be replenished, connecting a net 403 from a new roll 409 with the end of a net 403 from an empty roll, thereby allowing continuous operating of the algae cultivation plant as shown.

Figure 12:
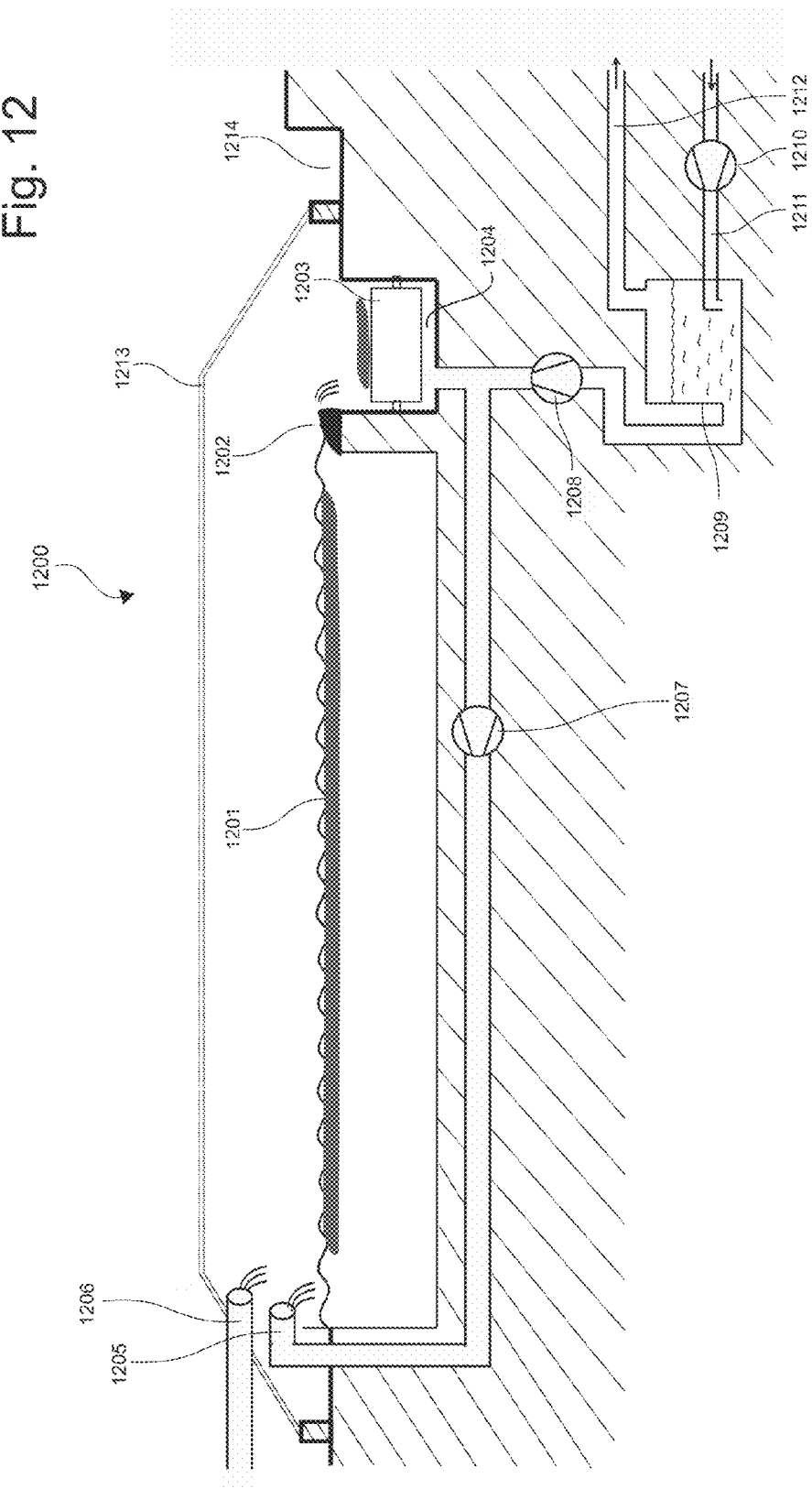
FIG. 12 shows an algae cultivation pond which is suitable for use in flat terrain.

An alternative harvesting technique is disclosed with reference to FIG. 12. An algae cultivation pond 1200 is provided, having a recirculation inlet 1205 and a freshwater inlet 1206 on one end of algae cultivation pond 1200. On the opposite end of algae cultivation pond 1200 is an overflow rim 1202. The top edge of overflow rim 1202 is at the lowest point of the wall surrounding the algae cultivation pond and thereby establishes the maximum water level of water in algae cultivation pond 1200. Overflow rim 1202 is fin-shaped, to allow algae slick 1201 to easily flow across it. Any excess water entering algae cultivation pond 1200 through recirculation inlet 1205 or freshwater inlet 1206 flows over overflow rim 1202 into collector reservoir 1204. Disposed within collector reservoir 1204 is conveyor belt 1203.

In a continuous operating mode of an algae cultivation plants as illustrated in FIG. 12 water constantly circulates within algae cultivation pond 1200 by pumping water through pump 1207 from collector reservoir 1204 through pipes and recirculation inlet 1205 into algae cultivation pond 1200. Any water loss is replenished by adding water through freshwater inlet 1206. Water added through freshwater inlet 1206 may be rich in nutrients that are required to foster growth of algae slick 1201. Circulation of water through algae cultivation pond 1200 causes algae slick 1201 to move with the circulating water over overflow rim 1202 and onto conveyor belt 1203. Conveyor belt 1203 separates algae mass from water, and transports the algae for further processing.

In a burst operating mode, the water level in algae cultivation pond 1200 is kept below overflow rim 1202 during a growth phase of algae slick 1201. When algae slick 1201 is ready for harvest, water is added into algae cultivation pond 1200 through freshwater inlet 1206. Additionally, water may be caused to circulate by pumping water through pump 1207 from collector reservoir 1204 to recirculation inlet 1205. The flow of water from through algae cultivation pond 1200 from inlets 1205 and 1206 to overflow rim 1202 causes algae slick 1201 to flow over overflow rim 1202 onto conveyor belt 1203. Conveyor belt 1203 transports the algae for further processing. To provide optimal growth conditions of algae slick 1201 water that is saturated with carbon dioxide can be injected into the water circulation of algae cultivation pond 1200 from an underground water reservoir 1209 through pump 1208. Flue gas which is rich in carbon dioxide is inserted into underground water reservoir 1209 through compressor 1210. Excess carbon dioxide which does not dissolve into the water in underground water reservoir 1209 returns through return pipe 1212 back to the flue. To protect the algae in algae cultivation pond 1200 a transparent cover 1213 is provided, which prevents contaminants such as leafs, dust, or rain from entering algae cultivation pond 1200. Transparent cover 1213 is mounted such, that rain water is directed into a trench 1214, which directs the rain water away from algae cultivation pond 1200, thereby maintaining close control over the environment in algae cultivation pond 1200.

An alternative algae cultivation plant is illustrated in FIG. 13. Algae cultivation pond 1300 is provided. Through water inlet 1305 water can be pumped into algae cultivation pond 1300, e.g. water that is rich in nutrients that are required for algae slick 1301 to grow in algae cultivation pond 1300. Located at one end of algae cultivation pond 1300 is an overflow rim 1303. Located behind overflow rim 1303 is a conveyor belt 1304. Algae slick 1301 can be harvested manually by pulling a floating rake 1302 across algae cultivation pond 1300 towards overflow rim 1303. Floating rake 1302 pulls algae slick 1301 across overflow rim 1303 onto conveyor 1304. From there, algae slick 1301 is transported by conveyor 1304 for further processing. Located around conveyor 1304 are water drains or recirculation pipes (not illustrated) to drain water that is pulled with algae slick 1301 onto conveyor 1304.

Figure 14:
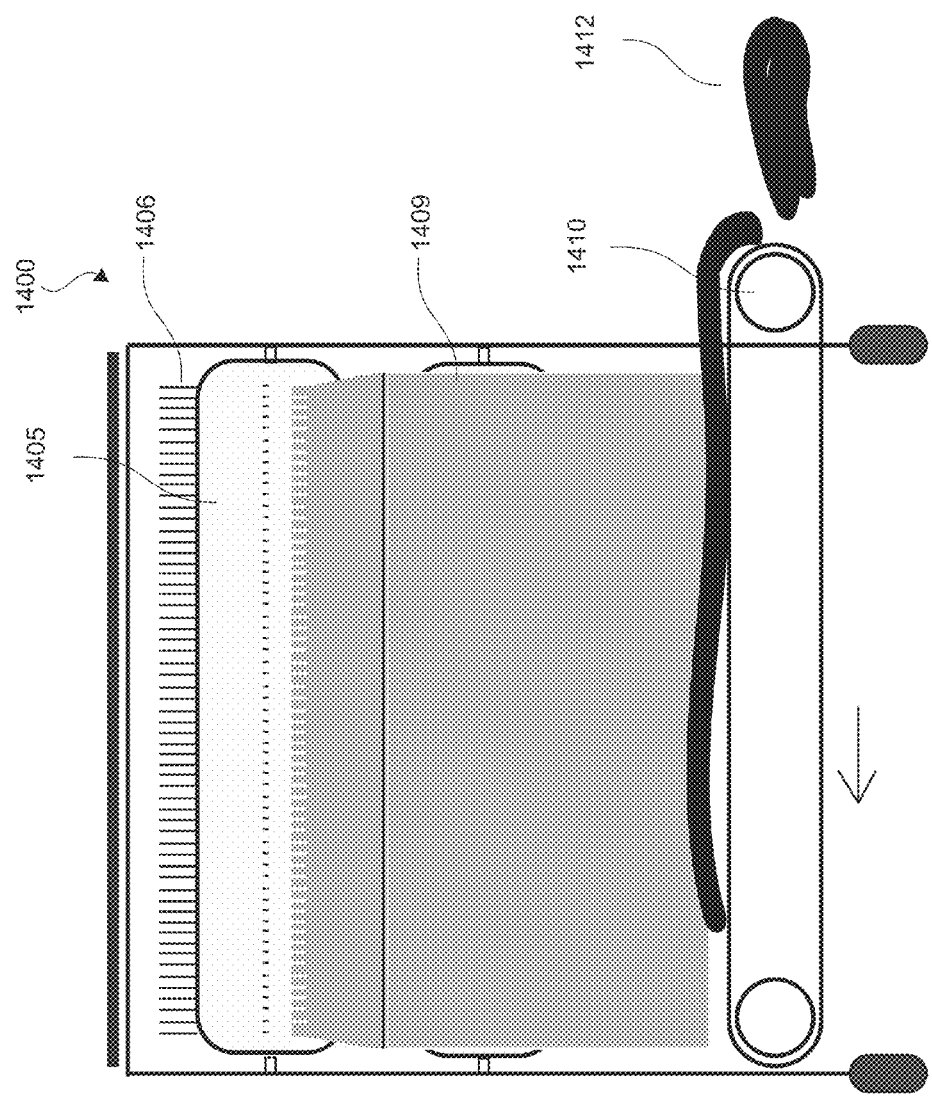

An alternative approach of harvesting algae in an algae cultivation pond is the use of an algae harvesting machine 1400 as shown in FIG. 14. Algae harvesting machine 1400 is preferably used in algae cultivation ponds 1420 having a width that is only slightly wider than the width of algae harvesting machine 1400. Algae harvesting machine 1400 comprises a frame 1402, which rests on wheels 1403. Wheels 1403 allow algae harvesting machine 1400 to move forward and backward in algae cultivation pond 1420.

An algae slick 1401 floating in algae cultivation pond 1420 can be automatically harvested with algae harvesting machine 1400. Algae slick 1401 is picked up by a rotating harvesting barrel 1404. Harvesting barrel 1404 comprises circumferentially and axially spaced spikes 1421 which lift algae mass 1401 out of the water in algae cultivation pond 1420 as algae harvesting machine 1400 moves along cultivation pond 1420. From harvesting barrel 1404 algae slick 1401 is transferred to conveyor barrel 1405, which conveys algae mass 1401 from harvesting barrel 1404 to slide 1409. Slide 1409 utilizes a comb-shaped end, through which spikes 1406 of conveyor barrel 1405 can pass. Algae slick 1401 is separated from conveyor barrel 1405 and slides along slide 1409 onto conveyor belt 1410. Conveyor belt 1410 transports algae slick for further processing outside algae cultivation pond 1420.

Algae harvesting machine 1400 is powered electrically through photovoltaic cells 1411 located on top of frame 1402. Since algae slick 1401 needs sun to grow, and algae harvesting machine 1400 needs sunlight to charge batteries (not shown) through photovoltaic cells 1411, photovoltaic cells 1411 can be dimensioned such, that they supply just enough energy to facilitate harvesting algae slick 1401 that has grown when exposed to the same sunlight as photovoltaic cells 1411.

Algae harvesting machine 1400 further comprises an exterior light sensor 1407 above algae slick 1401 and a submersed light sensor 1408 below algae slick 1401. The difference in sunlight sensed by exterior light sensor 1407 and submersed light sensor 1408 indicated the thickness of algae slick 1401, and can be used to determined the best speed of algae harvesting machine 1400.

While the present invention has been described with reference to exemplary embodiments, it will be readily apparent to those skilled in the art that the invention is not limited to the disclosed or illustrated embodiments but, on the contrary, is intended to cover numerous other modifications, substitutions, variations and broad equivalent arrangements that are included within the spirit and scope of the following claims.

What is claimed is:

1. An insulation panel comprising
a plurality of honeycomb-shaped chambers forming a body made of material comprising at least 20% of dried algae mass, the honeycomb-shaped chambers being sealed by a foil or a board which is laminated onto the body.

2. The insulation panel as in claim 1 wherein the sealed chambers are evacuated.

3. The insulation panel as in claim 1, configured to be thermally insulating, wherein one or more honeycomb-shaped chambers are filled with algae mass.

4. The insulation panel as in claim 1, configured to be noise attenuating, wherein one or more honeycomb-shaped chambers are filled with a noise attenuating material.

5. The insulation panel as in claim 4, wherein the noise attenuating material is a sand.

6. The insulation panel as in claim 4, wherein the noise attenuating material is configured to absorb energy when compressed by sound waves.

7. The insulation panel as in claim 6, wherein the noise attenuating material is a liquid foam or a gel containing gas bubbles.

8. The insulation panel as in claim 1 comprising a first plurality of honeycomb shaped chambers forming an upper body covered by a top foil and a second plurality of honeycomb shaped chambers forming a lower body covered by a bottom foil,
wherein the lower body is attached to the upper body such that the honeycomb-shaped chambers of the lower body are offset against the honeycomb-shaped chambers of the upper body.

9. The insulation panel as in claim 8,
wherein the first plurality of honeycomb shaped chambers forming the upper body is filled with a noise attenuating material and
wherein the second plurality of honeycomb shaped chambers forming the lower body is filled with a heat insulating material.

10. The insulation panel as in claim 8,
wherein the first plurality of honeycomb shaped chambers forming the upper body is filled with a noise attenuating material and wherein the second plurality of honeycomb shaped chambers forming the lower body is filled with a heat insulating material.

11. The insulation panel as in claim 8,
the honeycomb-shaped chambers of the lower body are offset against the honeycomb-shaped chambers of the upper body by ½ of their size.

\* \* \* \* \*